(12) United States Patent
Filiberti

(10) Patent No.: US 11,684,804 B2
(45) Date of Patent: Jun. 27, 2023

(54) PATIENT SUPPORTS FOR MEDICAL TREATMENTS

(71) Applicant: Varian Medical Systems International AG, Steinhausen (CH)

(72) Inventor: Reto W. Filiberti, Baar (CH)

(73) Assignee: Siemens Healthineers International AG, Steinhausen (CH)

(*) Notice: Subject to any disclaimer, the term of this patent is extended or adjusted under 35 U.S.C. 154(b) by 265 days.

(21) Appl. No.: 16/837,939

(22) Filed: Apr. 1, 2020

(65) Prior Publication Data

US 2021/0308483 A1 Oct. 7, 2021

(51) Int. Cl.
| | |
|---|---|
| A61B 6/03 | (2006.01) |
| A61B 6/00 | (2006.01) |
| G21K 5/08 | (2006.01) |
| H05G 1/00 | (2006.01) |
| A61N 5/10 | (2006.01) |
| A61B 6/04 | (2006.01) |

(52) U.S. Cl.
CPC .............. *A61N 5/107* (2013.01); *A61B 6/032* (2013.01); *A61B 6/0407* (2013.01); *A61N 5/1077* (2013.01); *A61B 6/0492* (2013.01); *A61N 5/1068* (2013.01); *A61N 2005/1091* (2013.01)

(58) Field of Classification Search
CPC ................... A61N 5/1077; A61N 5/107; A61N 2005/1091; A61N 5/1068; A61N 5/1049; A61N 5/1067; A61N 5/01; A61N 5/1048; A61N 5/1069; A61N 2005/1055; A61N 5/1065; A61N 5/103; A61B 6/032; A61B 6/0487; A61B 6/0407; A61B 6/0492; A61B 6/0464; A61B 6/4447; A61B 6/469; A61B 6/488; A61B 6/5205; A61B 6/4078; A61B 6/486; A61B 6/04; A61B 6/5217; A61B 6/0421; A61B 6/5264; A61B 6/5223; A61B 6/027; A61B 6/504; A61B 6/541; A61B 6/547; A61B 6/503; A61B 6/5258; G01R 33/4808
USPC ............... 378/20, 65, 208, 209, 68; 600/427
See application file for complete search history.

(56) References Cited

U.S. PATENT DOCUMENTS

| | | | |
|---|---|---|---|
| 5,464,013 A * | 11/1995 | Lemelson | .......... A61K 49/0004 378/68 |
| 6,405,072 B1 * | 6/2002 | Cosman | ................. A61B 90/16 606/130 |
| 6,888,919 B2 | 5/2005 | Graf | |
| 7,649,981 B2 | 1/2010 | Seppi et al. | |

(Continued)

*Primary Examiner* — Irakli Kiknadze
(74) *Attorney, Agent, or Firm* — Harness, Dickey & Pierce, P.L.C.

(57) ABSTRACT

A patient supporting device includes: a base; a positioner; a platform having a first end and a second end; and a controller; wherein the positioner is operable by the controller to place the platform at one of a first plurality of possible positions or at one of a second plurality of possible positions, wherein in any of the first plurality of possible positions, the second end of the platform is closer to one of a left side and a right side of a treatment machine; wherein in any of the second plurality of possible positions, the second end of the platform is closer to another one of the left side and the right side; and wherein a size of a first spatial region defined by the first plurality of possible positions is different from a size of a second spatial region defined by the second plurality of possible positions.

21 Claims, 12 Drawing Sheets

(56) References Cited

U.S. PATENT DOCUMENTS

| | | | | |
|---|---|---|---|---|
| 7,860,550 | B2* | 12/2010 | Saracen | A61B 6/548 |
| | | | | 5/601 |
| 8,542,797 | B2* | 9/2013 | Roberts | A61N 5/1049 |
| | | | | 378/65 |
| 8,655,429 | B2* | 2/2014 | Kuduvalli | B25J 9/1682 |
| | | | | 600/407 |
| 8,731,634 | B2* | 5/2014 | Birman | A61B 6/547 |
| | | | | 600/407 |
| 9,498,167 | B2* | 11/2016 | Mostafavi | A61N 5/10 |
| 9,687,200 | B2* | 6/2017 | Maurer, Jr. | A61B 6/032 |
| 11,045,376 | B2* | 6/2021 | Yano | A61G 13/04 |
| 11,083,420 | B2* | 8/2021 | Suga | A61B 6/0407 |
| 2012/0020449 | A1* | 1/2012 | Yan | A61N 5/107 |
| | | | | 378/65 |
| 2018/0085603 | A1* | 3/2018 | Kruesi | A61B 5/704 |
| 2018/0146932 | A1* | 5/2018 | Suga | A61N 5/1049 |

* cited by examiner

PATIENT SUPPORTS FOR MEDICAL TREATMENTS

FIELD

This application relates generally to medical systems, and more specifically, to medical systems with patient supports.

BACKGROUND

Radiation therapy has been employed to treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Sometimes, in a radiation treatment procedure, a plurality of treatment sessions may be performed. In each treatment session, a radiation source may be placed at various prescribed gantry angles to thereby deliver radiation beam towards a target tissue from different angles. As a result of delivering radiation towards the target tissue from a plurality of different angles, a sufficient radiation dose may be delivered to the target tissue to thereby treat the target tissue, while surrounding healthy tissue may be protected.

Methods and apparatuses for positioning a patient relative to a treatment machines are described herein.

SUMMARY

Patient supporting devices that are supported on rails have the advantage of achieving desirable ranges of treatment. However, inventor of the subject disclosure discovered that installing rails for supporting translatable patient supporting devices are very costly because the rails need to be manufactured with extreme precision, and also because the installation of such rails needs to be very precise. Installation of rails for patient supporting devices are also labor intensive. The patient supporting device and its mounting geometry with respect to a treatment machine described herein are advantageous over patient supporting devices supported on rails. This is because the patient supporting device has a fix-mounted base that is significantly easier and more cost effective to implement than patient supporting devices on rails. Also, the mounting geometry of the patient supporting device described herein limits the rotational travel range of a platform of the patient supporting device in one direction (i.e., on either the left or right side of a treatment machine) by fixedly mounting the base of the patient supporting device asymmetrically in front of a treatment machine (e.g., by an offset distance). This feature, while may be considered as undesirable in the field of patient support devices (and is therefore unintuitive), saves a high amount of equipment and installation cost and installation time, while unexpectedly achieving desirable ranges of treatment as discovered by the inventor of the subject disclosure. Despite not having a full travel range (i.e., +/−90° from center axis of treatment machine), the patient supporting device described herein with asymmetric travel range (e.g., −90° and +45° from center axis of treatment machine) can still support most of the treatment cases, while saving a considerable amount of manufacturing cost and installation time. In some cases, the kinematic concept described herein and the mounting position of the base of the patient supporting device can be selected such that even with the asymmetric rotation travel range, a full range of treatment (e.g., anywhere from skull to pelvis) can be achieved. Furthermore, the patient supporting device and its mounting configuration described herein are advantageous because they can be used with smaller treatment room, or room with certain geometric limitations. The patient supporting device and its mounting geometry with respect to a treatment machine described herein may be utilized in many different treatment systems, such as treatment system with ring gantry machine, treatment system with proton treatment machine, etc.

A patient supporting device for supporting a patient, includes: a base configured to be fixedly coupled to a room; a positioner mechanically coupled to the base; a platform mechanically coupled to the positioner, wherein the platform has a first end and a second end opposite the first end; and a controller configured to operate the positioner; wherein the positioner is operable by the controller to place the platform at one of a first plurality of possible positions, wherein in any of the first plurality of possible positions, the first end of the platform is in or below a treatment space, and the second end of the platform is closer to one of a left side and a right side of a treatment machine; wherein the positioner is also operable by the controller to place the platform at one of a second plurality of possible positions, wherein in any of the second plurality of possible positions, the first end of the platform is in or below the treatment space, and the second end of the platform is closer to another one of the left side and the right side of the treatment machine; and wherein a size of a first spatial region defined by the first plurality of possible positions is different from a size of a second spatial region defined by the second plurality of possible positions.

Optionally, the first spatial region has an angular range of more than 60°.

Optionally, the first spatial region has an angular range that is anywhere between 70° and 110°.

Optionally, the second spatial region has an angular range of less than 60°.

Optionally, the second spatial region has an angular range that is anywhere between 35° and 55°.

Optionally, the positioner includes: a first member having a first end and a second end, wherein the first end of the first member is rotatably coupled to the base so that the first member is rotatable relative to the base about a first vertical axis; a second member having a first end and a second end, wherein the first end of the second member is rotatably coupled to the second end of the first member so that the second member is rotatable relative to the first member about a second vertical axis; wherein the platform is rotatably coupled to the second end of the second member so that the platform is rotatable relative to the second member about a third vertical axis.

Optionally, the second member comprises a first member portion and a second member portion, the first member portion comprising the first end of the second member, the second member portion comprising the second end of the second member, wherein the second member portion is rotatably coupled to the first member portion so that the second member portion is rotatable relative to the first member portion about a first horizontal axis.

Optionally, the platform is rotatably coupled to the second member portion so that the platform is rotatable relative to the second member portion about a second horizontal axis.

Optionally, a rotation of the platform relative to the second member portion about the second horizontal axis, and a rotation of the second member portion relative to the first member portion about the first horizontal axis, are synchronized to move the platform vertically.

Optionally, the platform comprises a longitudinal axis, and the positioner is configured to tilt the platform about the longitudinal axis.

Optionally, the patient supporting device further includes one or more cameras coupled to the platform.

Optionally, the platform is detachably coupled to the positioner.

Optionally, the patient supporting device further includes a user interface configured for allowing an operator to enter one or more commands to control a positioning and/or movement of the platform.

Optionally, the positioner is also operable by the controller to place a first part of the platform below an isocenter of the treatment machine, the first part of the platform being closer to the first end of the platform than to the second end of the platform.

Optionally, the controller is configured to operate the positioner to move the platform during delivery of treatment energy by the treatment machine.

Optionally, the controller is configured to operate the positioner to move the platform in synchronization with a treatment energy out of the treatment machine to implement extended source-to-axis distance (SAD), reduced SAD, or variable SAD.

A medical system includes the patient supporting device, and the treatment machine, wherein the patient supporting device is configured to place the patient at a treatment position with respect to the treatment machine.

Optionally, the positioner is operable by the controller to place a first part of the platform under an isocenter, and to move the second end of the platform along a horizontal path while maintaining the first part of the platform under the isocenter.

Optionally, the patient supporting device is configured to place the platform at an orientation with respect to the treatment machine, and wherein when the platform is at the orientation, a longitudinal axis of the platform forms an acute angle with respect to a machine axis that extends from a front of the treatment machine to a back of the treatment machine.

Optionally, the treatment machine is configured to rotate an energy output while the platform is at the orientation.

Optionally, the medical system further includes an imaging machine, wherein the patient supporting device is configured to place the patient at an imaging position with respect to the imaging machine.

Optionally, the treatment machine and the imaging machine are in a side-by-side configuration.

Optionally, the treatment machine and the imaging machine are in a front-to-front configuration.

Optionally, the imaging machine comprises a CT machine, a x-ray machine, a fluoroscope, a MRI machine, an ultrasound device, a PET machine, a SPECT machine, or a PET-CT machine.

Optionally, the patient supporting device is configured to move the platform in accordance with a first movement scheme when the platform is in a first coordinate system associated with the treatment machine, and to move the platform in accordance with a second movement scheme when the platform is in a second coordinate system associated with the imaging machine, the second movement scheme being different from the first movement scheme.

Optionally, the treatment machine comprises a radiation treatment machine.

Optionally, the radiation treatment machine comprises a ring gantry.

Optionally, the radiation treatment machine comprises an arm having an energy output and a collimator.

Optionally, the treatment machine comprises a proton treatment machine.

A medical method includes: providing a patient supporting device having a base, a positioner, a controller, and a platform for supporting a patient, wherein the base is fixed with respect to a room accommodating the patient supporting device, wherein the positioner is coupled between the base and the platform, and wherein the platform comprises a first end and a second end opposite the first end; and operating the positioner, by the controller, to place the platform at one of a first plurality of possible positions, or at one of a second plurality of possible positions; wherein in any of the first plurality of possible positions, the first end of the platform is in or below a treatment space, and the second end of the platform is closer to one of a left side and a right side of a treatment machine; wherein in any of the second plurality of possible positions, the first end of the platform is in or below the treatment space, and the second end of the platform is closer to another one of the left side and the right side of the treatment machine; and wherein a size of a first spatial region defined by the first plurality of possible positions is different from a size of a second spatial region defined by the second plurality of possible positions.

Optionally, the positioner comprises a first member rotatable relative the base about a first vertical axis, a second member rotatable relative to the first member about a second vertical axis, wherein the platform is rotatable relative to the second member about a third vertical axis.

Optionally, the positioner is operated to rotate the platform relative to the second member about the third vertical axis.

Optionally, the positioner is operated to rotate the second member relative to the first member about the second vertical axis.

Optionally, the positioner is operated to rotate the first member relative to the base about the first vertical axis.

Optionally, the positioner is operated to move the platform vertically.

Optionally, the positioner is operated to rotate the platform about a vertical axis while a first part of the platform is maintained under an isocenter.

Optionally, the platform is placed at an orientation with respect to the treatment machine, and wherein when the platform is at the orientation, a longitudinal axis of the platform forms an acute angle with respect to a machine axis that extends from a front of the treatment machine to a back of the treatment machine.

Optionally, the medical method further includes rotating an energy output at the treatment machine while the platform is at the orientation.

Optionally, the positioner is operated by the controller to place the patient at an imaging position with respect to an imaging machine.

Optionally, the treatment machine and the imaging machine are in a side-by-side configuration.

Optionally, the treatment machine and the imaging machine are in a front-to-front configuration.

Optionally, the imaging machine comprises a CT machine, a x-ray machine, a fluoroscope, a MRI machine, an ultrasound device, a PET machine, a SPECT machine, or a PET-CT machine.

Optionally, the medical method further includes delivering treatment radiation by the treatment machine.

Optionally, the medical method further includes delivering a proton beam by the treatment machine.

Optionally, the medical method further includes: operating the positioner, by the controller, to move the platform in accordance with a first movement scheme when the platform is in a first coordinate system associated with the treatment machine; and operating the positioner, by the controller, to move the platform in accordance with a second movement scheme when the platform is in a second coordinate system associated with the imaging machine, the second movement scheme being different from the first movement scheme.

Optionally, the positioner is operated, by the controller, to move a first part of the platform below an isocenter of the treatment machine, wherein the first part of the platform is closer to the first end of the platform than to the second end of the platform.

Optionally, the positioner is operated by the controller to move the platform during delivery of treatment energy by the treatment machine.

Optionally, the positioner is operated by the controller to move the platform in synchronization with a treatment energy out of the treatment machine to implement extended source-to-axis distance (SAD), reduced SAD, or variable SAD.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Figure 1:
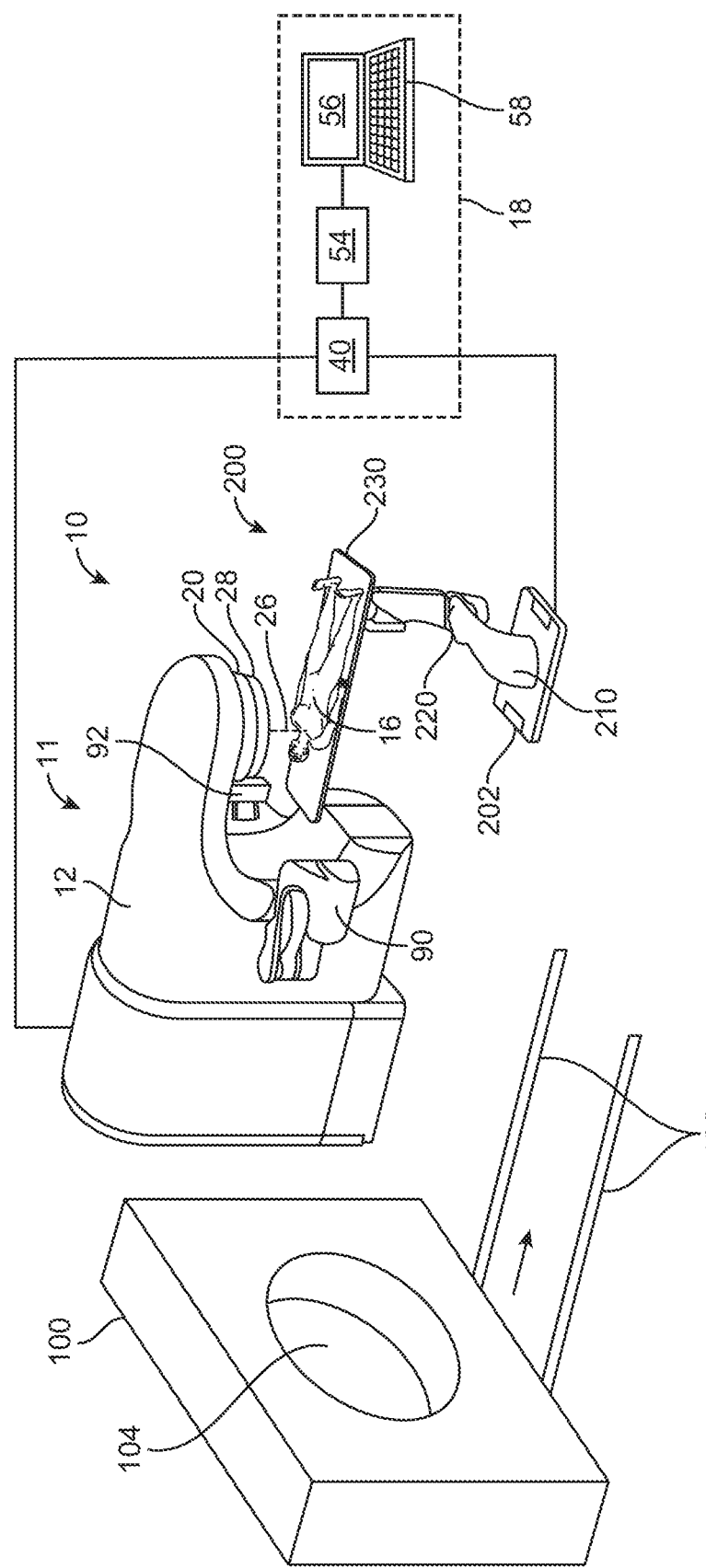
FIG. 1 illustrates a medical system having a treatment machine for delivering treatment energy, an imaging machine, and a patient supporting device in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not to have all the aspects or advantages shown. An aspect or an advantage described in conjunction with a particular embodiment is not necessarily limited to that embodiment and can be practiced in any other embodiments even if not so illustrated.

FIG. 1 illustrates a medical system 10 including a treatment machine 11 for delivering treatment radiation. The treatment machine 11 includes a gantry 12 in a form of an arm. The treatment machine 11 also includes an energy output 20 that outputs a beam 26 of radiation towards a patient 16 while the patient 16 is supported on platform 230, and a collimator system 28 for controlling and shaping the beam 26. The energy output 20 can be configured to output a cone beam, a fan beam, or other shapes of radiation beams in different embodiments. Also, as used in this specification, the term "radiation" may refer to photons, electrons, protons, ions, etc., or any form of energy output.

In the illustrated embodiments, the treatment machine 11 includes a treatment radiation source for providing treatment radiation energy. In other embodiments, in addition to being a treatment radiation source, the radiation source 20 can also be a diagnostic radiation source for providing diagnostic energy. In such cases, the treatment machine 11 will include an imager located at an operative position relative to the energy output 20 (e.g., under the platform 14). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source is able to generate X-ray radiation at a plurality of photon energy levels within a range anywhere between approximately 10 keV and approximately 20 MeV. Radiation sources capable of generating X-ray radiation at different energy levels are described in U.S. Pat. No. 6,888,919, entitled "RADIOTHERAPY APPARATUS EQUIPPED WITH AN ARTICULABLE GANTRY FOR POSITIONING AN IMAGING UNIT," filed on May 3, 2005, and U.S. Pat. No. 7,649,981, entitled "MULTI-ENERGY X-RAY SOURCE," issued on Jan. 19, 2010. In further embodiments, the radiation source can be a diagnostic radiation source. In the illustrated embodiments, the energy output 20 is rotatably coupled to the gantry 12. In other embodiments, the energy output 20 may be located within a bore (instead of being located at an arm).

The medical system 10 also includes a control system 18 for controlling an operation of the treatment machine 11. In the illustrated embodiments, the control system 18 includes a processor 54, such as a computer processor, coupled to a control 40. The control system 18 may also include a monitor 56 for displaying data and an input device 58, such as a keyboard and/or a mouse, or a touchscreen, for inputting data. In the illustrated embodiments, the gantry 12 is rotatable about the patient 16, and during a treatment procedure, the gantry 12 rotates about the patient 16 (as in an archtherapy). The operation of the radiation source, the collimator system 28, and the gantry 12 (if the gantry 12 is rotatable), are controlled by the control 40, which provides power and timing signals to the radiation source and the collimator system 28, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

As shown in the figure, the platform 230 is a part of a patient supporting device 200. The patient supporting device 200 includes a base 202, a first member 210, a second member 220, and the platform 230. The patient supporting device 200 will be described in further detail below.

In some embodiments, the treatment machine 11 may optionally include one or more imaging devices. For example, as shown in FIG. 1, the treatment machine 11 may further include a x-ray source 90 and an imager 92 located opposite from the x-ray source 90. The x-ray source 90 and the imager 92 may be configured to image the patient 16 before a delivery of treatment energy (e.g., for patient setup), and/or during a treatment energy delivery session (e.g., between deliveries of radiation beams). In other embodiments, the treatment machine 11 may not include the x-ray source 90 and the imager 92.

It should be noted that the treatment machine 11 is not limited to the configuration described above, and that the treatment machine 11 may have other configurations in other embodiments. For example, in other embodiments, the treatment machine 11 may have a different shape. In other embodiments, the energy output 20 of the treatment machine 11 may have different ranges of motions and/or degrees of freedom. For example, in other embodiments, the energy output 20 may be rotatable about the patient 16 completely through a 360° range, or partially through a range that is less than 360°. Also, in other embodiments, the energy output 20 is translatable relative to the patient 16. In further embodiments, the gantry 12 may be a ring gantry with a bore, and the energy output 20 may be located inside the bore of the gantry 12.

As shown in FIG. 1, the medical system 10 further includes an imaging machine 100. The treatment machine 11, the imaging machine 100, and the patient supporting device 200 are all accommodated in a same room in a facility. In the illustrated embodiments, the imaging machine 100 is moveable along rails 102. Accordingly, the relative position between the imaging machine 100 and the treatment machine 11 is selectively adjustable. Similarly, the relative position between the imaging machine 100 and the patient supporting device 200 is also selectively adjustable. During use, the patient supporting device 100 may be operated to place the patient 16 at an operative position with respect to the treatment machine 11 for treatment purpose, and/or at an operative position with respect to the imaging machine 100 for imaging purpose. For imaging purpose, the imaging machine 100 is moved along the rails 102 towards the patient supporting device 200. The patient supporting device 200 then moves the platform 230 to place the patient 16 in an operative position with respect to the imaging machine 100 for imaging purpose. In the illustrated example, the imaging machine 100 is a CT machine with a bore 104 for accommodating at least a part of the patient 16 for imaging. In other examples, the imaging machine 100 may be a x-ray machine, a fluoroscope, a MRI machine, an ultrasound device, a PET machine, a SPECT machine, or a PET-CT machine, etc.

In other embodiments, the imaging machine 100 may be fixedly mounted to a floor of a room, or may have wheels/rollers that allow the imaging machine 100 to be freely positioned and/or transported to any location. In such cases, the rails 102 are not required.

In the above embodiments, the rails 102 for the imaging machine 100 are illustrated as being rectilinear. In other embodiments, the rails 102 may have a curvilinear configuration. Also, in the above embodiments, the rails 102 are illustrated as being at the floor (e.g., they can be mounted on or in the floor). In other embodiments, the rails 102 may be mounted at the ceiling of the operating room. In further embodiments, the rails 120 may be mounted to a wall of the operating room. Regardless of where the rails are mounted, the imaging machine 100 is configured to translate (e.g., in a rectilinear path, in a curvilinear path, or both) within a room. Furthermore, instead of two rails, in other embodiments, the imaging machine 100 may be configured to move along only one rail, or more than two rails. In further embodiments, the rails 102 may not be required. For example, in further embodiments, the imaging machine 100 may have a plurality of wheels at its bottom for allowing it to move relative to the floor.

Figure 2A:
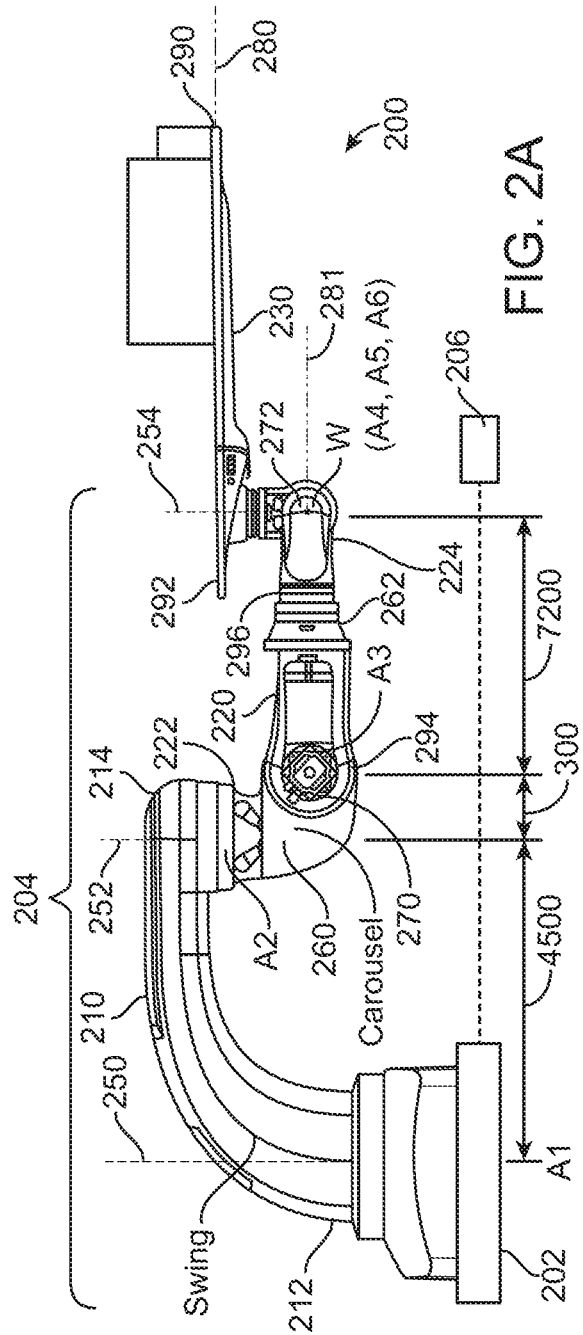
FIG. 2A illustrates the patient supporting device of FIG. 1.

FIG. 2A illustrates the patient supporting device 200 of FIG. 1. As shown in the figure, the patient supporting device 200 has a base 202, a positioner 204, a controller 206, and the platform 230. In the illustrated example, the positioner 204 includes a first member 210 with a first end 212 and a second end 214, and a second member 220 with a first end 222 and a second end 224. The base 202 is configured to be fixedly coupled to a room. For example, the base 202 may be configured to be anchored to a floor of a room in some embodiments. The first end 212 of the first member 210 is rotatably coupled to the base 202 so that the first member 210 is rotatable relative to the base 202 about a first vertical axis 250. The first end 222 of the second member 220 is rotatably coupled to the second end 214 of the first member 210 so that the second member is rotatable relative to the first member 210 about a second vertical axis 252. The platform 230 is rotatably coupled to the second end 224 of the second member 220 so that the platform 230 is rotatable relative to the second member 220 about a third vertical axis 254.

In the illustrated embodiments, the second member 220 has a first member portion 260 and a second member portion 262. The first member portion 260 is rotatably coupled to the second member portion 262 so that the first member portion 260 can rotate relative to the second member portion 262, or vice versa, about a first horizontal axis 270. The platform 230 is rotatably coupled to the second member portion 262 so that the platform 230 can rotate relative to the second member portion 262 about a second horizontal axis 272. During use, the platform 230 can rotate relative to the second member portion 262 about the second horizontal axis 272, and the second member portion 262 can rotate relative to the first member portion 260 about the first horizontal axis 270, in synchronization, so that the platform 230 can move vertically (e.g., up and/or down).

Also, in the illustrated embodiments, the platform 230 is configured to rotate about its longitudinal axis 280 and/or about another axis 281. In the illustrated embodiments, the second member portion 262 has a first segment 294 that is rotatably coupled to a second segment 296 such that the second segment 296 can rotate about the axis 281 relative to the first segment 294.

In the example shown in the figure, the first member 210 is in a form of an arm, and the second member 220 is also in a form of an arm. Also, the first member portion 260 may be considered to be a part of an arm, and the second member portion 260 may be considered to be another part of the arm. In other embodiments, the first member 210 may have other form and/or shape, and may not necessarily be an arm. Similarly, in other embodiments, the second member 220 may have other form and/or shape, and may not necessarily be an arm.

It should be noted that the positioner 204 is not limited to the configuration shown in FIG. 2A, and that the positioner 204 may have other configurations in other embodiments. For example, in other embodiments, the positioner 204 may have only one member, or may have more than two members. Also, in other embodiments, instead of moveably connecting the second member 220 below the first member 210 at the second end 214 of the first member 210, the second member 220 may be moveably connected to the second end 214 of the first member 210 above the first member 210. In further embodiments, the positioner 204 may provide fewer or more degrees of freedom compared to those shown in FIG. 2A.

The controller 206 of the patient positioning device 200 is configured to operate the positioner 204 to place the platform 230 in different positions. In some embodiments, the controller 206 may be implemented at the patient positioning device 200. In other embodiments, the controller 206 may be located away from the base 202 of the patient positioning device 200, and is in communication with the positioner 204 (e.g., via a wired connection or a wireless connection). Also, in some embodiments, the controller 206 of the patient positioning device 200 may be implemented as a part of the control 40 of the medical system 10. The controller 206 is configured to generate control signals to operate one or more components of the positioner 204 to thereby move the platform 230 to certain desired positions during a medical process. For example, the controller 206 may generate control signals to operate one or more motors, one or more driving units, etc., in the positioner 204 to thereby move different components of the positioner 204. In some embodiments, the controller 206 is configured to receive input from a treatment planning module, which processes a treatment plan for the patient 16 in order to obtain desired positions of the platform 230. The input from the treatment planning module indicates the desired positions of the platform 230 to be achieved during certain parts of the medical process. The controller 206 then interprets the input, and generates corresponding control signals to operate the positioner 204 so that the desired positions of the platform 230 can be achieved.

Figure 3:
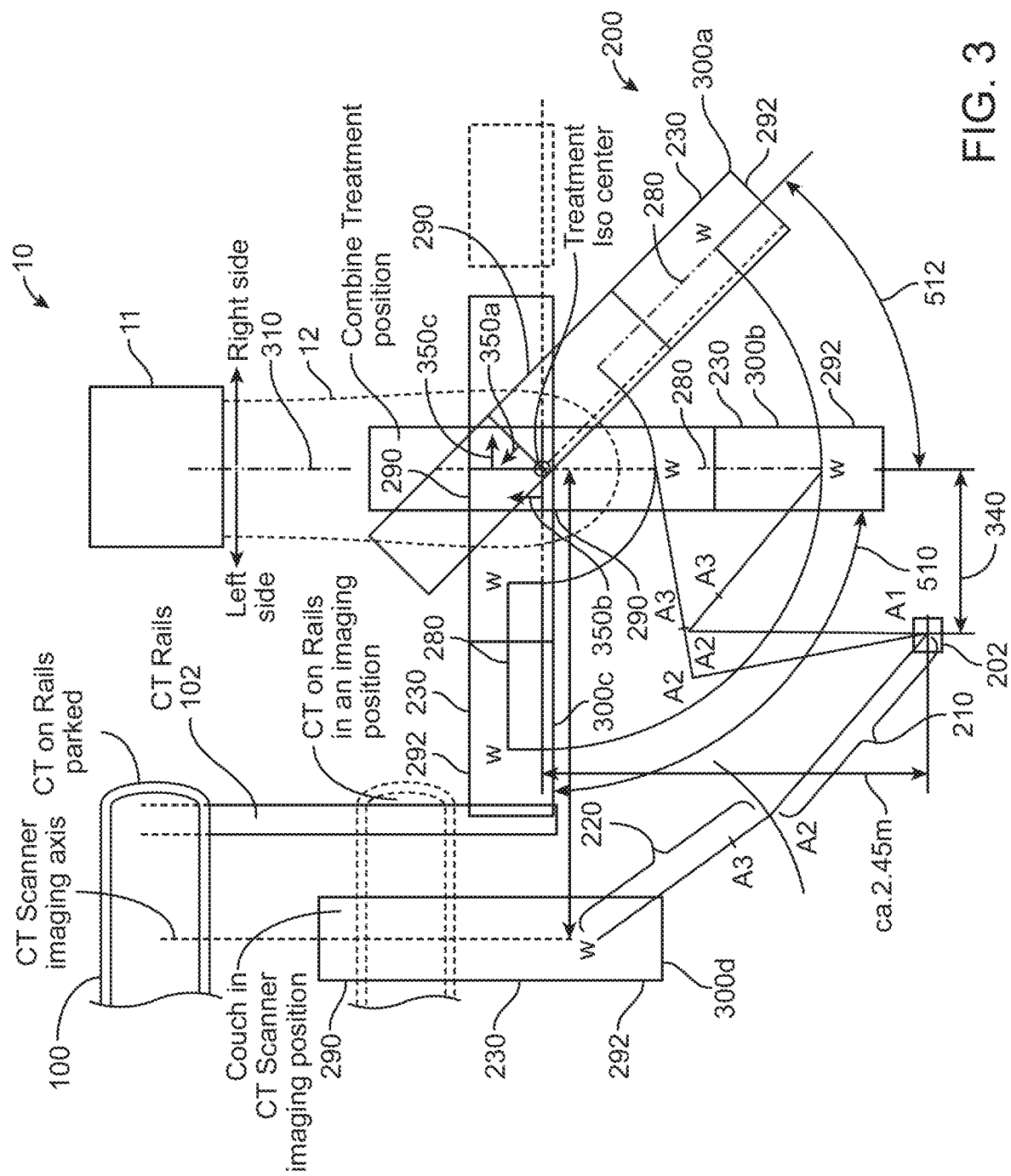
FIG. 3 illustrates the patient supporting device of FIG. 1, particularly showing exemplary ranges of motion of a platform of the patient supporting device of FIG. 2A.

FIG. 3 illustrates the medical system 10 of FIG. 1, particular showing exemplary ranges of motion of the platform 230 of the patient supporting device 200 of FIG. 2A. In the figure, the first member 210 is represented as a line between nodes A1 and A2, and the second member 220 is represented as a line between node A2 and node W), which allows possible positions of the first and second members 210, 220 to be visualized more clearly. The line between nodes A2 and A3 represents the first member portion 260 of the second member 220. The nodes A1, A2, A3, W are also shown in FIG. 2A. In FIG. 3, node A1 indicates the location of the base 202 of the patient supporting device 200, which is fixedly mounted with respect to a floor. Node A2 is the connection between the second end 214 of the first member 210 and the first end 222 of the second member 220. The node W coincides with the vertical axis 254 or axis 272 (shown in FIG. 2A). In FIG. 3, the gantry 12 of the treatment machine 11 is illustrated as dotted line for clarity purpose.

As shown in FIG. 3, the platform 230 supporting the patient may be selectively placed at one of a plurality of positions 300a-300c for allowing the treatment machine 11 to deliver treatment energy towards the patient. The platform 230 may also be selectively placed at position 300d for allowing the imaging machine 100 to image the patient. Although only three positons 300a-300c with respect to the treatment machine 11 are shown, it should be understood that the platform 230 may be placed at other positions with respect to the treatment machine 11. For example, when the platform 230 is in any of the positions 300a-300c, the platform 230 may optionally be translated along its longitudinal axis 280, as represented by the arrows 350a-350c. In the illustrated embodiments, the positioning of the platform 230 is accomplished by the positioner 204 that is operated by the controller 206 (shown in FIG. 2A). As shown in FIG. 3, when positioning the patient for treatment purpose, a part (that is closer to the first end 290 than to the second end 292) of the platform 230 may be placed in an operative position (e.g., below an isocenter) of the treatment machine 11, as illustrated in the various positions 300a-300c of the platform 230. Also, as shown in the figure, while the part of the platform 230 that is closer to the first end 290 is placed in the operative position with respect to the treatment machine 11 (e.g., in or below a treatment space), the second end 292 of the platform 230 may be selectively placed at many different positions (as illustrated by the different orientations of the platform 230 in the different positions 300a-300c). As shown in the figure, because the base 202 of the patient supporting device 200 is offset (by distance 340) with respect to a center of the treatment machine 11, and due to the geometry and degrees of freedom of the patient supporting device 200, the range 510 of the possible positions for the second end 292 of the platform 230 when the platform 230 is closer to the left side than to the right side of the treatment machine 11, is different from the range 512 of the possible positions for the second end 292 of the platform 230 when the platform 230 is closer to the right side than to the left side of the treatment machine 11. The left side and right side of the treatment machine 11 is separated by a plane 310 extending through a center of the treatment machine 11. As illustrated in the figure, the range 510 is about 90°, and the range 512 is about 45°. In other embodiments, the ranges 510, 512 may have other values. For example, in other embodiments, the range 510 may be an angular range that is any value higher than 60°, such as anywhere between 70° and 110°. Also, in other embodiments, the range 512 may be an angular range that is any value less than 60°, such as anywhere between 35° and 55°. In further embodiments, the range 512 may be less than 40°, less than 30°, less than 20°, less than 10°, or 0°.

As shown in FIG. 3, the positioner 206 is operable by the controller 204 to place the platform 230 at one of a first plurality of possible positions (such as position 300c), wherein in any of the first plurality of possible positions, the first end 290 of the platform 230 is in or below a treatment space, and the second end 292 of the platform 232 is closer to one of a left side and a right side of a treatment machine 11. The positioner 206 is also operable by the controller 204 to place the platform 230 at one of a second plurality of possible positions (such as position 300a), wherein in any of the second plurality of possible positions, the first end 290 of the platform 230 is in or below the treatment space, and the second end 292 of the platform 230 is closer to another one of the left side and the right side of the treatment machine 11. In the illustrated embodiments, a size of a first spatial region defined by the first plurality of possible positions (i.e., the positions of the second end 292 when the platform 230 is at the left side) is different from a size of a second spatial region defined by the second plurality of possible positions (i.e., the positions of the second end 292 when the platform 230 is at the right side). As shown in the figure, the size of the first spatial region has the angular range 510, and the size of the second spatial region has the angular range 512.

Figure 2B:
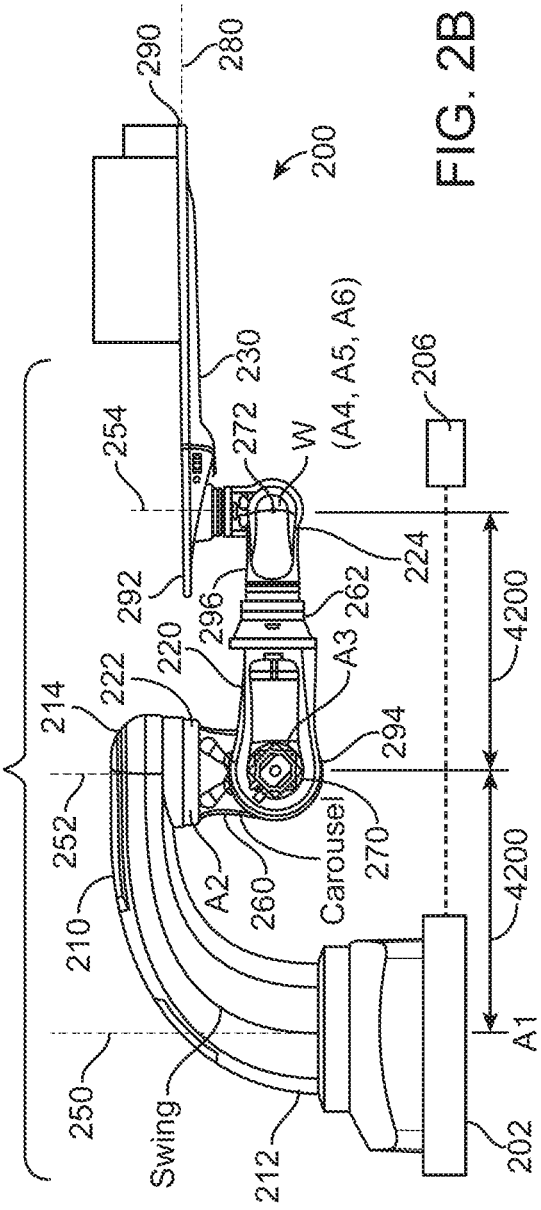
FIG. 2B illustrates a variation of the patient support device of FIG. 1.
Figure 4:
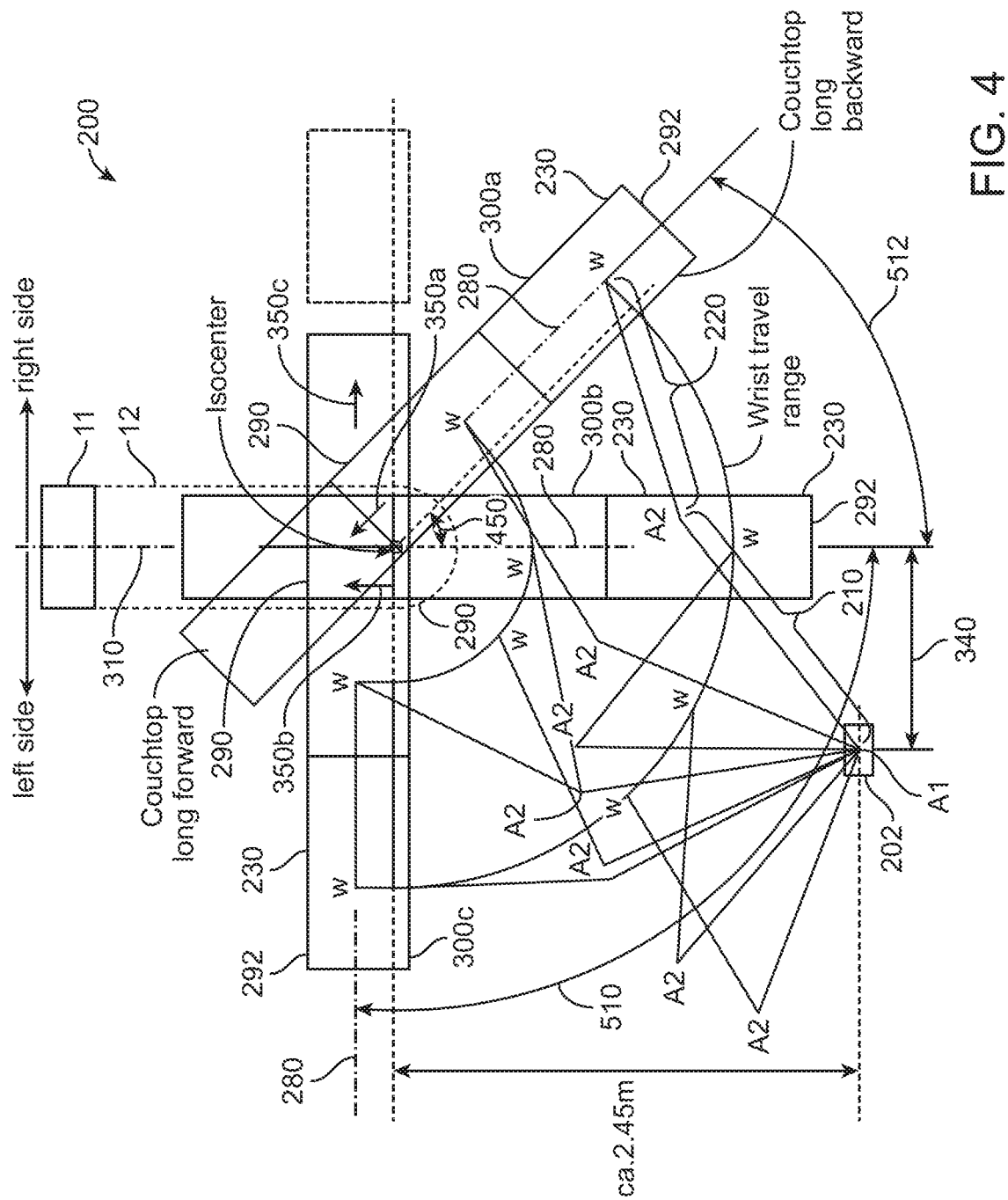
FIG. 4 illustrates exemplary ranges of motion of a platform of the patient supporting device of FIG. 2B.

It should be noted that the patient supporting device 200 should not be limited to the above embodiments, and that the patient supporting device 200 may have other configurations in other embodiments. For example, as shown in FIG. 2B, the horizontal axis 270 about which the second member portion 262 rotates relative to the first member 260 may be align with the vertical axis 252, so that the nodes A2, A3 are aligned. FIG. 4 illustrates exemplary ranges of motion of the platform 230 of the patient supporting device 200 of FIG. 2B. As shown in the figure, the platform 230 can be selectively placed at various positions 300a-300c, like those described with reference to FIG. 3. However, unlike FIG. 3, the diagram in FIG. 4 does not have lines representing the first member portion 260. This is because the first member portion 260 in the patient supporting device 200 of FIG. 2B is oriented vertically, with the node A2 and A3 aligning vertically. Accordingly, in FIG. 4, node A3 (not shown) is below node A2. As shown in the figure, because the base 202 of the patient supporting device 200 is offset (by distance 340) with respect to a center of the treatment machine 11, and due to the geometry and degrees of freedom of the patient supporting device 200, the range 510 of possible positions for the second end 292 of the platform 230 on the left side of the treatment machine 11 (while the first end 290 is in the operative position with respect to the treatment machine 11—e.g., in or below a treatment space), is different from the range 512 of possible positions for the second end 292 of the platform 230 on the right side of the treatment machine 11 (while the first end 290 is in the operative position with respect to the treatment machine 11—in or below a treatment space).

Figure 5A:
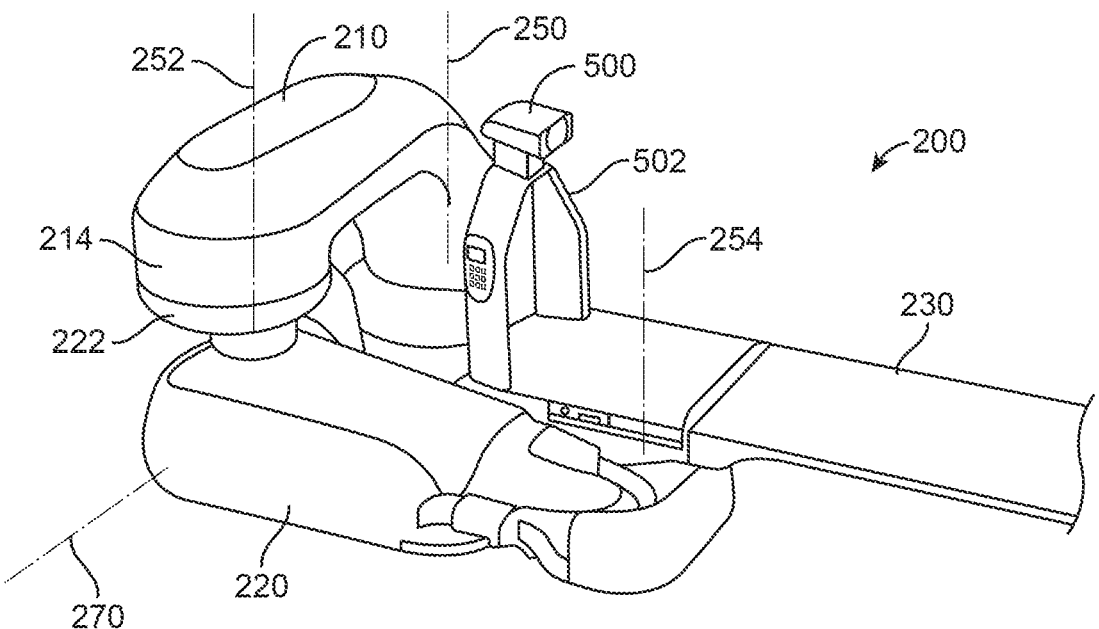
FIGS. 5A-5B illustrate a variation of the patient supporting device of FIG. 2B.
Figure 5B:
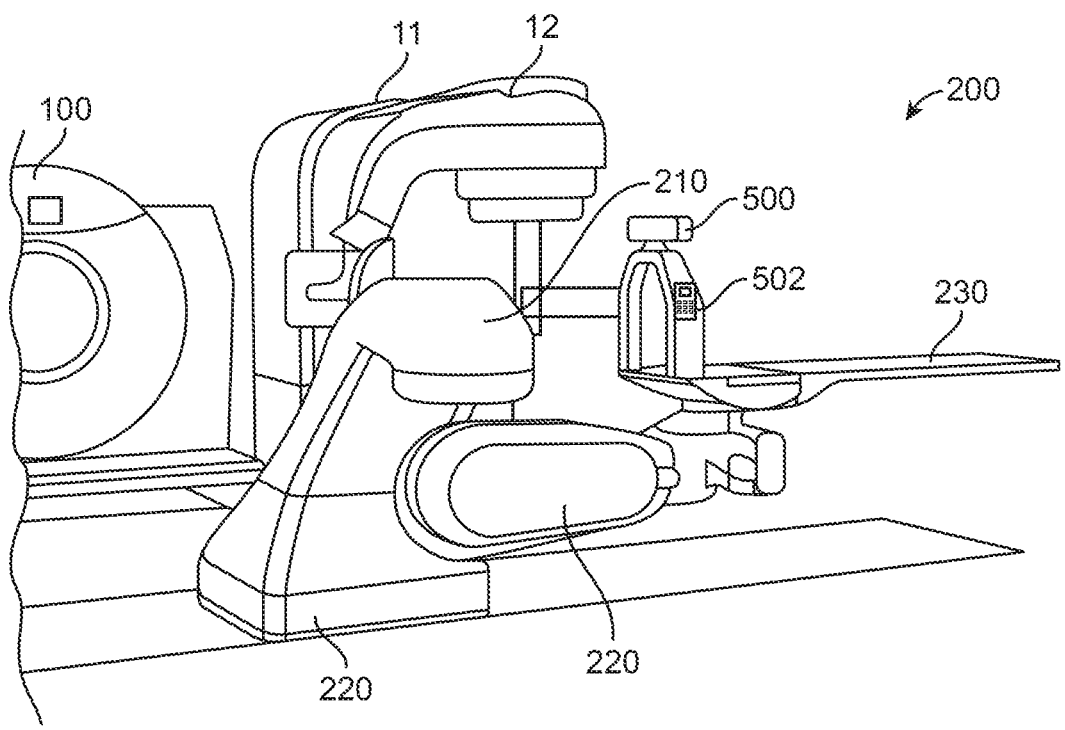

FIGS. 5A-5B illustrate a variation of the patient supporting device 200 of FIG. 2B. The patient supporting device 200 in FIGS. 5A-5B is the same as that shown in FIG. 2B, except that the shapes of the base 202, the first member 210, and the second member 220 are different from those shown in FIG. 2B. In the illustrated embodiments of FIGS. 5A-5B, the patient supporting device 200 further includes a camera 500 mounted to a frame 502. The frame 502 is coupled to the platform 230 of the patient supporting device 200. The camera may be an optical camera, a depth-sensing camera, or both.

Figure 6A:
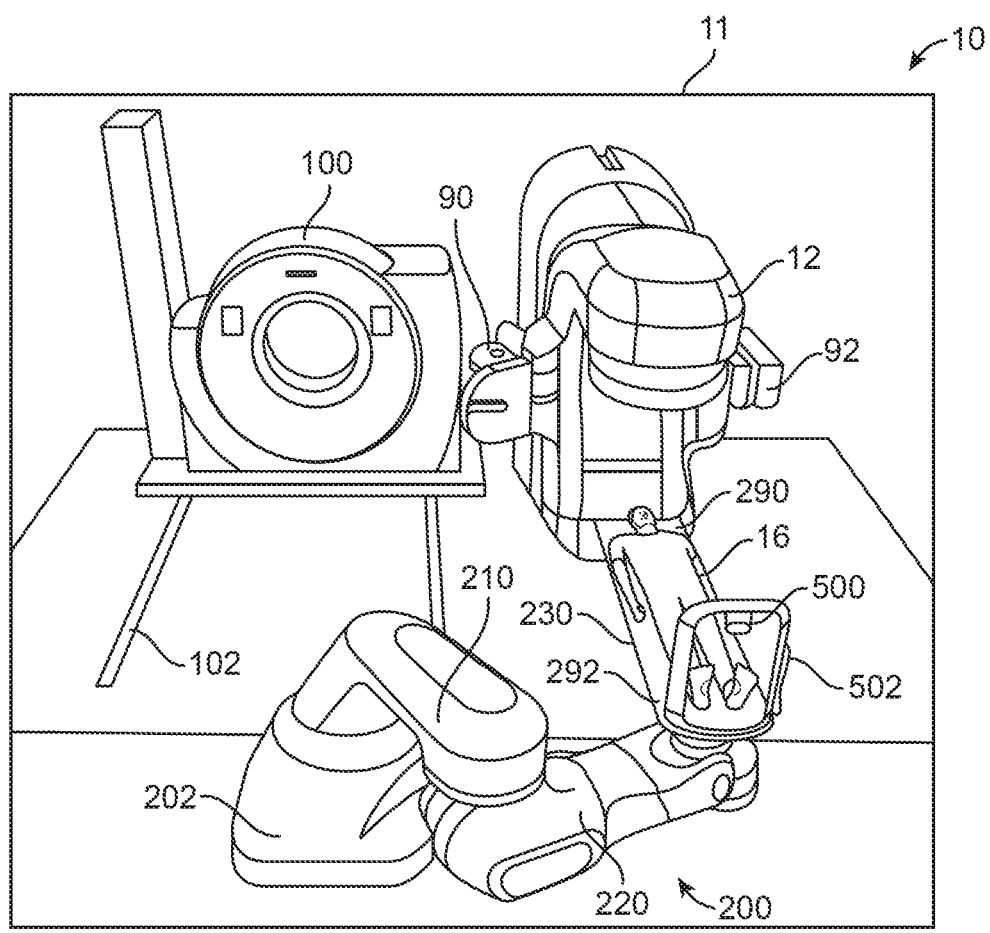
FIG. 6A-6C illustrate a variation of the medical system of FIG. 1, having the patient supporting device of FIGS. 5A-5B, particularly showing the platform being placed in different positions with respect to the treatment machine.
Figure 6B:
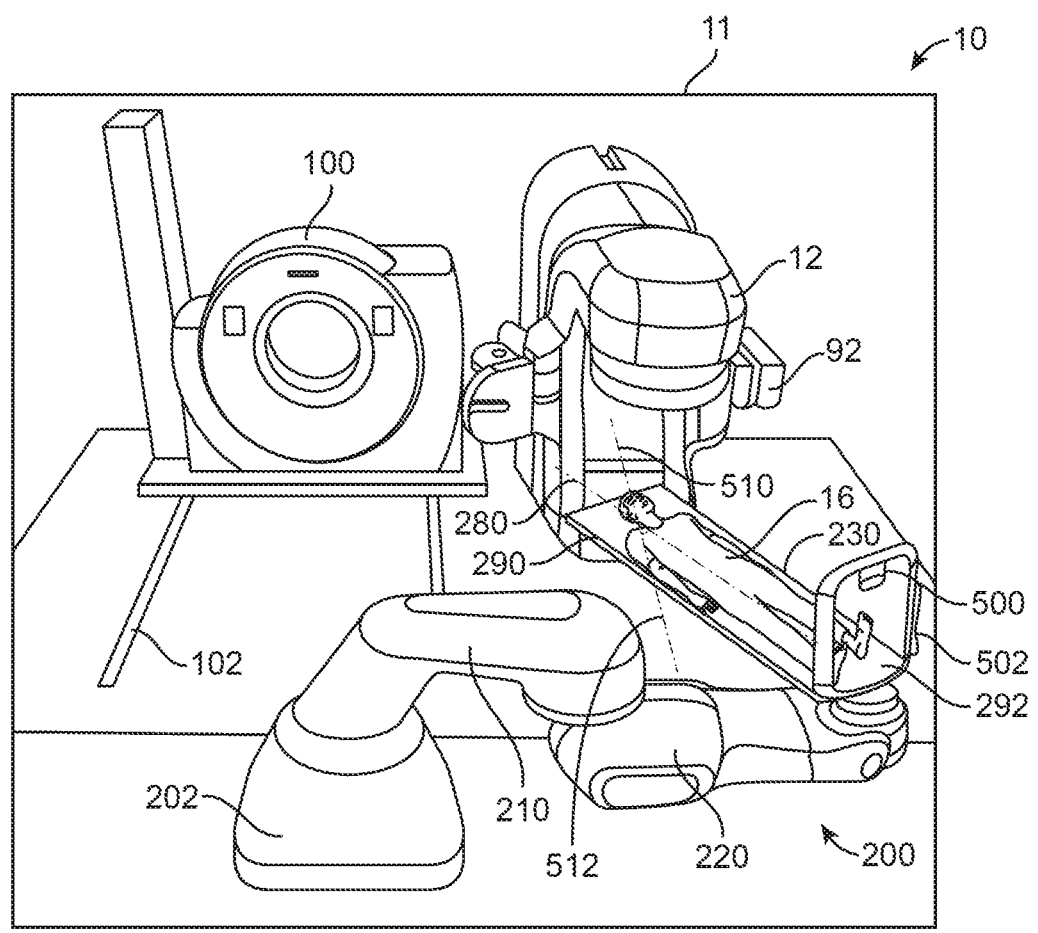
Figure 6C:
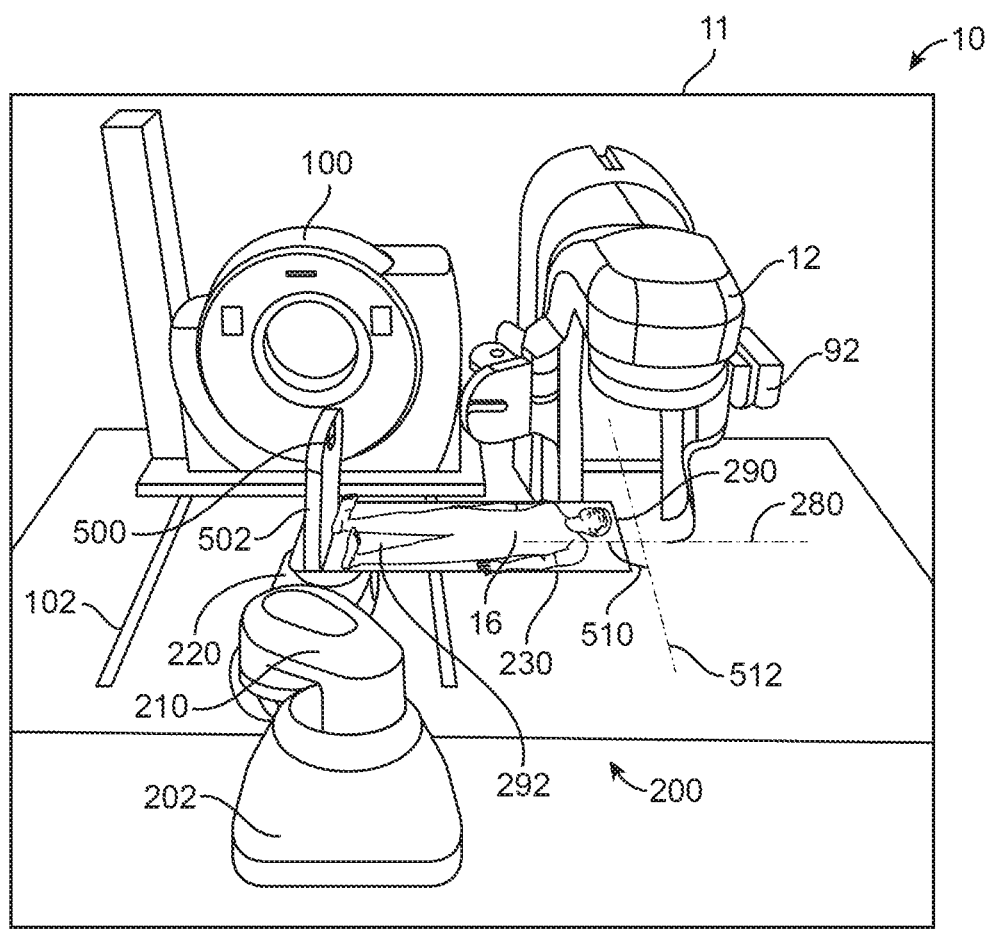

FIGS. 6A-6C illustrates a variation of the medical system 10 of FIG. 1, particularly showing the various possible positions of the platform 230 of the patient positioning device 200 of FIGS. 5A-5B. In particular, FIG. 6A illustrates the platform 230 of the patient positioning device 200 being placed at an operative position with respect to the treatment machine 11. In the operative position, the first end 290 of the platform 230 is in or below a treatment space of the treatment machine 11. A treatment space may be defined as any spatial region at which treatment energy can be delivered. Also, in such operative position, the longitudinal axis of the platform 230 is approximately parallel (e.g., forming an angle that is 0°+/−10° with respect) to a machine axis of the treatment machine 11. When the platform 230 is placed at the position shown in the figure, the treatment machine 11 can deliver treatment energy towards the patient from a plurality of different gantry angles. For example, the energy output 20 of the treatment machine 11 may be rotated partially or completely around the patient 16 to deliver treatment energies from different angles. The position of the platform 230 shown in FIG. 6A corresponds with the position 300b of the platform 230 shown in FIG. 4.

FIG. 6B illustrates the platform 230 of the patient positioning device 200 being placed at another position with respect to the treatment machine 11. In such position, the first end 290 of the platform 230 is in or below a treatment space 280 of the treatment machine 11. Also, in such position, the longitudinal axis of the platform 230 forms an angle 510 with respect to a machine axis 512, wherein the angle 510 is approximately 45° (e.g., 45°+/−10°). When the platform 230 is placed at the position shown in the figure, the treatment machine 11 can deliver treatment energy towards the patient from a plurality of different gantry angles. For example, the energy output 20 of the treatment machine 11 may be rotated partially or completely around the patient 16 to deliver treatment energies from different angles. The position of the platform 230 shown in FIG. 6B corresponds with the position 300a of the platform 230 shown in FIG. 4.

FIG. 6C illustrates the platform 230 of the patient positioning device 200 being placed at another operative position with respect to the treatment machine 11. In such operative position, the first end 290 of the platform 230 is in or below a treatment space of the treatment machine 11. Also, in such operative position, the longitudinal axis 280 of the platform 230 forms an angle 510 with respect to a machine axis 512, wherein the angle 510 is approximately 90° (e.g., 90°+/−20°). When the platform 230 is placed at the position shown in the figure, the treatment machine 11 can deliver treatment energy towards the patient from a plurality of different gantry angles. For example, the energy output 20 of the treatment machine 11 may be rotated at least partially around the patient 16 to deliver treatment energies from different angles. The position of the platform 230 shown in FIG. 6C corresponds with the position 300c of the platform 230 shown in FIG. 4.

In the above embodiments, the medical system 10 has been described as having the treatment machine 11 and the imaging machine 100 in a side-by-side configuration. In the side-by-side configuration, both a front of the treatment machine 11 and a front of the imaging machine 100 are facing the same direction. During use, the patient supporting device 200 may be configured to place the patient at a treatment position with respect to the treatment machine 11, and also at an imaging position with respect to the imaging machine 100. For example, before a treatment session begins, the patient supporting device 200 may place the patient at the imaging position to allow the imaging machine 100 to image the patient. The image(s) from the imaging machine 100 may be used to confirm the position and shape of target (e.g., tumorous tissue), and/or be used to perform patient setup. After the image(s) is obtained, the patient supporting device 200 may then move the patient from the imaging position to the treatment position, to thereby allow the treatment machine 11 to deliver treatment energies towards the patient. During treatment, if desired, the patient supporting device 200 may move the patient from the treatment position to the image position to allow the imaging machine 100 to obtain additional image(s) of the patient.

The additional image(s) may be used to determine position and/or shape of target, which in turn, may be used to update or modify a treatment plan.

In some embodiments, the patient supporting device 200 may be configured to make motions in multiple different coordinate systems corresponding with respective different machines. For example, the controller 206 of the patient supporting device 200 may be configured to operate the patient supporting device 200 to move in a first path within a first coordinate system (e.g., one for the treatment machine 11), and to operate the patient supporting device 200 to move in a second path different from the first path within a second coordinate system (e.g., one for the imaging machine 100). In some embodiments, the controller 206 may be configured to operate the positioner 204 to move the platform 230 in accordance with a first movement scheme when the platform 230 is in a first coordinate system associated with the treatment machine 11; and to operate the positioner 204 to move the platform 230 in accordance with a second movement scheme when the platform 230 is in a second coordinate system associated with the imaging machine 100, the second movement scheme being different from the first movement scheme.

Figure 7:
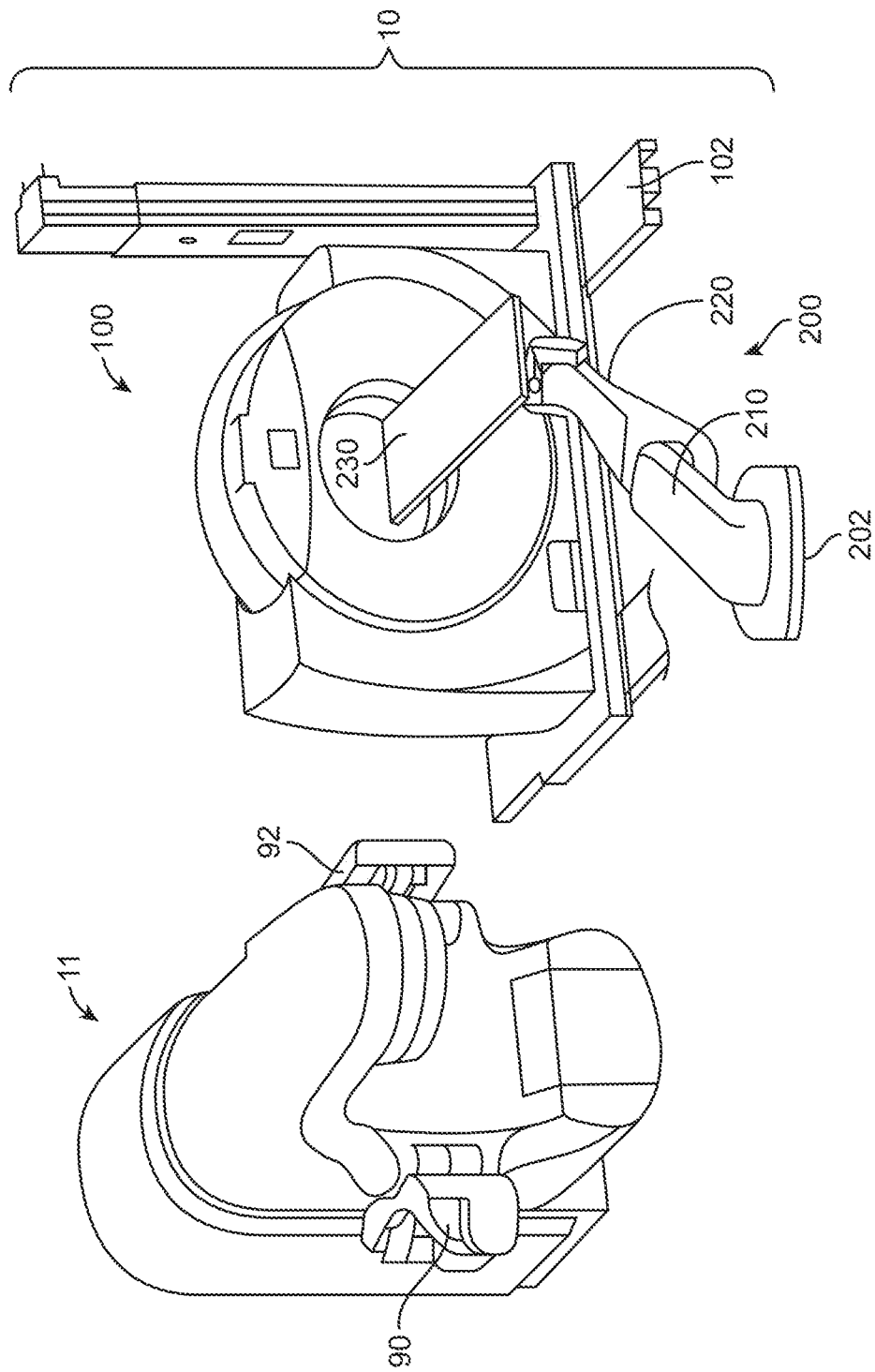
FIG. 7 illustrates another medical system having a treatment machine, an imaging machine, and a patient supporting device.

In the above embodiments, the base 202 of the patient supporting device 200 is illustrated as being fixedly mounted offset (by distance 340) towards the left side of the treatment machine 11. The distance 340 may be at least 40 cm, at least 50 cm, at least 60 cm, at least 70 cm, at least 80 cm, at least 90 cm, at least 100 cm, at least 110 cm, at least 120 cm, at least 130 cm, at least 140 cm, or higher than 150 cm. In other embodiments, the base 202 of the patient supporting device 200 may be fixedly mounted offset towards the right side of the treatment machine 11 by the distance 340. In such cases, the imaging device 100 may be placed towards the right side of the treatment machine 11. FIG. 7 illustrates an example of such configuration. The arrangement of the treatment machine 11, the imaging machine 100, and the patient supporting device 200 in FIG. 7 is essentially a mirror configuration as that shown in FIG. 6A.

As illustrated in the above embodiments, the patient supporting device 200 and its mounting configuration are advantageous because the patient supporting platform 230 can be positioned by the positioner 204 to place the patient at a variety of positons and orientations with respect to the treatment machine 11. In the embodiments in which the treatment room also has the imaging machine 100, the platform 230 can also be positioned by the positioner to place the patient in an imaging space for imaging by the imaging machine 100. Also, in some embodiments, in combination with the movement of the energy output 20 of the treatment machine 11, the various degrees of movement of the patient supporting device 200 allow treatment energies to be delivered to the patient from many different angles.

The patient supporting device 200 and its mounting geometry with respect to a treatment machine described herein are advantageous over patient supporting devices supported on rails. This is because the patient supporting device 200 with the fix-mounted base is significantly easier and more cost effective to implement than patient supporting devices on rails. Installing rails for supporting translatable patient supporting devices are very costly because the rails need to be manufactured with extreme precision, and also because the installation of such rails needs to be very precise. Installation of rails for patient supporting devices are also labor intensive. Limiting the rotational travel range of the platform 230 in one direction (i.e., on either the left or right side of the treatment machine 11) by fixedly mounting the base 202 of the patient supporting device 200 asymmetrically in front of a treatment machine (e.g., by an offset distance) save a high amount of equipment and installation cost and installation time, while achieving desirable ranges of treatment. Despite not having a full travel range (i.e., +/−90° from center axis of treatment machine), the patient supporting device 200 with asymmetric travel range (e.g., −90° and +45° from center axis of treatment machine) can still support most of the treatment cases, while saving a considerable amount of manufacturing cost and installation time. In some cases, the kinematic concept described herein and the mounting position of the base 202 can be selected such that even with the asymmetric rotation travel range, a full range of treatment (e.g., anywhere from skull to pelvis) can be achieved.

Furthermore, the patient supporting device 200 and its mounting configuration described herein are advantageous because they can be used with smaller treatment room, or room with certain geometric limitations. The patient supporting device 200 and its mounting geometry with respect to a treatment machine described herein may be utilized in many different treatment systems, such as treatment system with ring gantry machine, treatment system with proton treatment machine, etc.

In the above embodiments, the asymmetric rotational range of the platform results in rotational ranges 510, 512 that are different for the left and right sides of the treatment machine 11. As illustrated in the above embodiments, such asymmetric rotational range may be achieved by providing the patient supporting device 200 with certain degrees of freedom while fixedly mounting its base 202 in an offset configuration with respect to a center line of the treatment machine 11. Accordingly, the limitation of the range 152 is based on mechanical and geometric limitations. In other embodiments, the limitation of the range may be achieved using logic control. For example, in other embodiments, the patient supporting device 200 may be mounted in front of the treatment machine 11 with the base 202 aligned with the center line of the treatment machine 11. In such cases, the asymmetric rotational ranges 510, 512 of the platform 230 may be achieved using logic control, such as via programming and/or via using input, which prescribes user desired values for the ranges 510, 512. In one implementation, a user interface may be provided that allows a user to enter desired values for the rotational ranges 510, 512. This feature may be helpful in many scenarios. For example, if the base 202 is placed too close to a wall of a treatment room, the user may enter a smaller value for one of the ranges 510, 512 that corresponds to the side of the room where the wall is located. This allows the platform 230 to have a limited rotational range to avoid the platform 230 colliding with the wall of the room. In some embodiments, one of the rotational range 510, 512 may be less than 45°, such as 30°, 20° 10°, 0°, etc.

It should be noted that in one or more embodiments described herein, a movement of the platform 230 may be achieved by moving the platform 230 relative to the second member 220, moving the second member 220 relative to the first member 210, moving the first member 210 relative to the base 202, or any combination of the foregoing. In some cases, if multiple components of the patient supporting device 200 are moved, the multiple components may be moved simultaneously. Alternatively, the multiple components may be moved in sequence such that one component is moved first, and then another component is moved afterwards. In either case, the energy output 20 may deliver treatment energy towards the patient while one or more of the components (e.g., the first member 210, the second member, 220, the platform 230, etc.) of the patient supporting device 200 are moving, and/or while the energy output 20 is moving. Alternatively, the energy output 20 may deliver treatment energy towards the patient when the components of the patient supporting device 200 have stopped moving, and when the energy output 20 has stopped moving. For example, when the platform 230 is moved along a path, the components of the patient supporting device 200 may stop moving at certain points along the path to allow the energy output 20 of the treatment machine 11 to deliver energies towards the patient. Similarly, when the energy output 20 of the treatment machine 11 is moved along a path, the energy output 20 may stop moving at certain points along the path to allow the energy output 20 to deliver energies towards the patient. Alternatively, the delivery of energies may occur simultaneously while the components of the patient supporting device 200 are moving, and/or while the energy output 20 of the treatment machine 11 is moving.

It should be noted that the movements and positioning of the various components of the patient supporting device 200 should not be limited to the examples described, and that the patient supporting device 200 may achieve other types of movements and positioning. For example, in other embodiments, the platform 230 may be translated vertically (e.g., up and/or down) while the orientation of the platform 230 is maintained. Such may be accomplished by synchronously rotating the second member 220 relative to the first member 210 about the first horizontal axis in a first direction, and simultaneously rotating the platform 230 relative to the second member 220 about the second horizontal axis in a second direction that is opposite the first direction. In other embodiments, the platform 230 may be translated horizontally along a path that corresponds with (e.g., parallel to) the center axis of the treatment machine 11. Such may be accomplished by synchronously rotating the first member 210 relative to the base 202 about the first axis 250 in a first direction, rotating the second member 220 relative to the first member 210 about the second axis 252 in a second direction opposite the first direction, and rotating the platform 230 relative to the second member 220 about the third axis 254 in the first direction. In still further embodiments, the platform 230 may be translated horizontally along any path that is parallel to the floor.

Also, in any of the embodiments described herein, the patient supporting device 200 may be configured to move at a speed that is sufficient for dynamic treatment. For example, the patient supporting device 200 may be configured to move in a path with a speed that corresponds (e.g., complements) with a motion speed of the treatment machine 11 (e.g., the speed of the rotating energy output 20) and/or the rate at which treatment energies are being delivered. Also, in some cases, the patient supporting device 200 may be configured to move with a sufficiently fast speed to allow the patient supporting device 200 to compensate for a breathing motion of the patient. For example, the patient supporting device 200 may be configured to move the patient in order to at least partially compensate for a breathing motion of the patient, thereby allowing breathing gating to be used to deliver treatment energies.

In addition, in any of the embodiments described herein, the patient supporting device 200 may be configured to move the platform 230 in synchronization or in correspondence with a movement or position of the energy output 20. For example, the platform 230 may be moved so that a point at the patient (e.g., an isocenter) is maintained at a certain prescribed distance or a certain prescribed range of distances from the energy output 20. Accordingly, regardless of the position of the energy output 20, the isocenter is maintained at a fixed distance or within a fixed distance range from the energy output 20. The movement of the platform 230 may be dynamically performed simultaneously with a movement of the energy output 20. Alternatively, the movement of the platform 230 may be performed after the energy output 20 has moved, so that the movements of the platform 230 and the energy output 20 are staggered. Furthermore, in some cases, the source-axis-distance (SAD) may be extended compared to the scenario in which the platform 230 is stationary and the energy output 20 is rotated around the platform 230. Such can be accomplished by moving the platform 230 in a direction that is away from the energy output 20, thereby increasing the SAD. During treatment, as the energy output 20 rotates around a space, the patient supporting device 200 also rotates the platform 230 around the same space in synchronization or in correspondence with the energy output 20. This allows the energy output 20 to always be aimed at a treatment target in the patient supported on the platform 230, while both the energy output 20 and the platform 230 on opposite sides of the space are being rotated in correspondence with each other. Alternatively, in some cases, the SAD may be reduced compared to the scenario in which the platform 230 is stationary and the energy output 20 is rotated around the platform 230. Such can be accomplished by moving the platform 230 in a direction that is towards the energy output 20, thereby reducing the SAD. In further cases, the SAD may be variable during a treatment session. For example, the platform 230 may be moved towards and/or away from the energy output 20 to achieve different SADs. This may occur during delivery of treatment energy by the energy output 20, and/or between deliveries of treatment energies. The different SADs may be achieved while the energy output 20 is at a same gantry angle, or may be achieved for different respective gantry angles of the energy output 20. Embodiments of the patient supporting device 200 and its mounting configuration described herein may be utilized to implement extended SAD treatments, reduced SAD treatments, or variable SAD treatments. Also, in some embodiments, the controller 206 may be configured to operate the positioner 204 to move the platform 230 in synchronization with a treatment energy out of the treatment machine 11 to implement extended SAD, reduced SAD, or variable SAD.

Furthermore, in one or more embodiments described herein, the controller 206 may be configured to operate the positioner 204 to move the platform 230 during delivery of treatment energy by the treatment machine 11. For example, the positioner 204 may translate the platform 230 along one or more axes, and/or rotate the platform 230 about one or more axes, while the treatment machine 11 delivers treatment energy towards the patient supported on the platform 230.

In the above embodiments, the treatment machine 11 has been described as having a rotatable arm that includes an energy output 20 and a collimator. In other embodiments, instead of the rotatable arm, the treatment machine 11 may have a ring gantry that carries the energy output 20. In such cases, during treatment, the patient supporting device 200 may be operated to place a part of the patient into a bore, and the ring gantry may be rotated around the patient to allow the energy output 20 to deliver treatment energies from different angles.

In addition, in any of the embodiments described herein, the platform 230 may be a removeable couch top. For example, the platform 230 may be detachably coupled to a connector that is at the second end of the second member 220. In some cases, the platform 230 may be removed from the rest of the patient supporting device 200, and the patient may be placed on top of the platform 230 for patient setup. The placement of the patient on the platform 230 may be performed in the treatment room where the patient supporting device 200 is located, or may be performed in another room. In one implementation, the patient may be positioned such that a reference location at the patient relative to the platform 230 is achieved. After that is set up, the platform 230 with the patient may then be attached to the connector at the patient supporting device 200. Furthermore, in some embodiments, the movement of the platform 230 with the patient to attach the platform 230 with the rest of the patient supporting device 200 may be performed automatically using a robotic device (e.g., a tool-changer).

In further embodiments, the patient supporting device 200 may also include one or more positional indicators for allowing a position of the patient supporting device 200 to be determined. For example, the patient supporting device 200 may include a positioning system that allows its position relative to some global coordinate system be determined. The positioning system may include one or more components at the platform 230, one or more components at the first member 210, one or more components at the second member 202, one or more components at the base 202, or any combination of the foregoing. The component may be a signal emitter, a signal receiver, a fiducial, a marker, etc. In other embodiments, a component may be a sensor for sensing a signal, or may be a fiducial that is configured for sensing, that can be used to derive a position.

In another example, the patient supporting device 200 may include multiple positional indicators at the respective moving parts (e.g., the first member 210, the first member portion 260 of the second member 220, the second member portion 262 of the second member 220, and the platform 230). The positional indicators may have respective energy sources for emitting positional energies (beacons), and there may be one or more detectors in the treatment room for detecting such positional energies. Based on the detected positional energies, a processing unit may then determine the positions and orientations of the various components of the patient supporting device 200. In other embodiments, the beacons may be passive devices. The processing unit for determining the positions and orientations of the components of the patient supporting device 200 may be implemented as a part of the controller 206 in some embodiments.

In another example, the positional indicators may include one or more markers at the platform 230, one or more markers at the first member 210, one or more markers at the second member 220, and one or more markers at the base 202. The markers may be configured to be detected using one or more cameras, or other types of sensing device(s).

Also, in any of the embodiments described herein, instead of having the platform 230 that is completely horizontal to support the entire patient horizontally, the platform 230 may have other configurations in other embodiments. For example, in other embodiments, the platform 230 may have a form of a chair to support the patient in an upright position. In one implementation, the platform 230 may have a first platform portion and a second platform portion that is rotatably coupled to the first platform portion. The platform portions may be operated so that both platform portions are oriented horizontally, thereby providing a completely horizontal supporting surface for supporting the patient horizontally. In another method of use, one of the platform portions may be rotated to be in an upright position, thereby creating a chair-like supporting structure for supporting the patient in an upright position.

Furthermore, in any of the embodiments described herein, the patient supporting device 200 may include one or more force and/or torque sensor for load measurement. In one implementation, the platform 230 may have a force sensor for measuring an amount of load being supported by the platform 230. The measurement may be transmitted to a processing unit, which calculates an amount of deflection resulted from such load. The processing unit may then operate the patient supporting device 200 (e.g., rotate the platform 230 about a horizontal axis that is perpendicular to the longitudinal axis of the platform 230) to compensate for such deflection. Because the patient supporting device 200 is configured to support load using cantilever-action, the amount of deflection due to heavy load supported by the platform 230 may be significant. The above feature may allow the deflection to be compensated. In other embodiments, the patient supporting device 200 may not support load using cantilever-action, and the deflection due to patient load on the platform 230 may not be significant.

In addition, in any of the embodiments described herein, the patient supporting device 200 and/or the treatment machine 11 may include one or more cameras (such as the camera 500 shown in FIGS. 5-6) for monitoring the patient. The one or more cameras may be used to sense one or more markers (e.g., one or more light emitting or light reflecting markers, one or more reference locations at the patient that function as marker(s), etc.). In some embodiments, the sensed markers may be used to determine a position of a patient part. For example, the sensed markers may be positionally related to a breathing movement of the patient. In such cases, the sensed markers may be processed by a processing unit, which determines one or more breathing phases of the patient. Also, in some embodiments, the one or more cameras may generate images for monitoring a position of the patient. The processing unit may process such images to ensure that the patient is at an intended position, and/or to provide collision detection and avoidance. It should be noted that one or more of the camera(s) may be a depth sensing camera. In one implementation, the patient supporting device 200 may include a depth sensing camera attached thereto. During use, the depth sensing camera detects a surface of the patient, and the processing unit generates a surface model representing the surface of the patient. While treatment is being performed, the patient supporting device 200 and the treatment machine 11 may move. The processing unit monitors objects next to the patient. If the processing unit determines that an object (e.g., the gantry 12 of the treatment machine 11) is getting too close to the patient (e.g., within a threshold distance from the surface model), the processing unit may then generates a warning signal and/or a control signal to stop or pause the treatment. For example, the processing unit may generate a control signal to stop a movement of the treatment machine 11 and/or a movement of the patient supporting device 200. The processing unit may also generate a control signal to stop a delivery of treatment energies by the treatment machine 11. In some cases, one or more proximity sensors may be employed to determine whether the patient is too close to component(s) of the treatment machine 11.

In addition, in some embodiments, the controller 206 of the patient supporting device 200 may be configured to avoid singularity problem. Singularity problem occurs when there are multiple sets of positions of the members of the positioner 204 that can achieve the same desired position of the platform 230. In some embodiments, such singularity problem may be avoided by providing certain constraint(s) for the operation of the positioner 204. For example, a constraint may be implemented in the controller 206 that limits the angular range between the first and second members 210, 220, such that only one set of positions for the members 210, 220 can provide a certain desired position for the platform 230.

Also, in the above embodiments, the treatment machine 11 has been described with reference to providing treatment radiation. In other embodiments, the treatment machine 11 may be configured to provide other types of treatment energy. For examples, in other embodiments, the treatment machine 11 may be configured to provide proton beam for proton therapy, treatment ultrasound energy, radiofrequency energy, etc. In addition, in other embodiments, the radiation source may be a proton source for delivering protons to treat a patient, an electron source for delivering electrons, or other types of particle source for delivering other types of particles for treating patient.

In any of the embodiments described herein, the operation of the patient supporting device 200 may be achieved using the controller 206 that generates control signals for causing one or more of the components (e.g., first member 210, second member 220, platform 230, etc.) of the patient supporting device 200 to move. The controller 206 may include circuitry and/or algorithm for generating the control signals. In some cases, the controller 206 may include a processing unit configured to receive and process a treatment plan, which prescribes the condition and/or the manner for moving the platform 230. The processing unit may generate the control signals based on parameters provided from the treatment plan. For example, the treatment plan may include parameters for indicating that the platform 230 be moved from position X to position Y when certain criteria are met. The criteria may be a position of the energy output of the treatment machine 11, a total accumulated dose delivered to the patient, an amount of dose delivered to target, an amount of dose delivered to critical organ, etc. In some embodiments, the controller 206 for the patient supporting device 200 may include a member control module for controlling movement of the first member 210 and/or the second member 220, and a platform control module for controlling a movement of the platform 230 relative to the second member 220. Also, in some embodiments, the treatment plan may prescribe the positions and orientations of the platform 230 to be accomplished at certain time points or certain conditions, and the controller 206 of the patient supporting device 200 may include an analysis module configured to determine which component(s) (e.g., the first member 210, the second member 220, the platform 230) to move and amount(s) of movement to accomplish the prescribed positions and orientations of the platform 230.

In any of the embodiments described herein, the patient supporting device 200 may also include a user interface for allowing an operator (user) to enter one or more commands to control a positioning and/or a movement of the platform 230. For example, in some cases, the user interface may include a keyboard and/or a mouse for allowing a user to prescribe a coordinate and/or an orientation for the platform 230. In response to the command(s) entered by the operator, the controller 206 may then operate the positioner 204 to place the platform 230 at the prescribed coordinate and/or orientation. As another example, the user interface may include a control-stick. In such cases, in response to the operator operating the control-stick in a certain direction (e.g., left, right, forward, backward), the platform 230 will move in the corresponding direction. In some embodiments, the control-stick may also include an up-button and a down-button for moving the platform 230 upward and downward, respectively. Furthermore, in some cases, the user interface may be implemented using an iphone, an ipad, a tablet, a laptop, or any of other communication devices. In some embodiments, the user interface may be in the same room with the patient supporting device 200. In other embodiments, the user interface and the patient supporting device 200 may be in separate respective rooms. Also, the user interface may be implemented at the patient supporting device 200, and may be a part of the patient supporting device 200. Furthermore, the user interface may have a first control interface (e.g., keyboard, mouse, screen, touchscreen, buttons, joystick, or any combination of the foregoing) at the patient supporting device 200, and a second control interface (e.g., keyboard, mouse, screen, touchscreen, buttons, joystick, or any combination of the foregoing) in a room that is different from the room in which the platform 230 is located. In such cases, an operator may selectively choose which of the user interfaces to use for controlling the positioning and/or the movement of the platform 230.

It should be noted that as used in this specification, the term "vertical" refers to an orientation that is approximately 90° (e.g., 90°±10°, and more preferably 90°±5°) with respect to a horizon or a horizontal floor. Also, as used in this specification, the term "horizontal" refers to an orientation that is approximately parallel (e.g., at 0°±10°, and more preferably 0°±5°) to a horizon or a horizontal floor.

Figure 8:
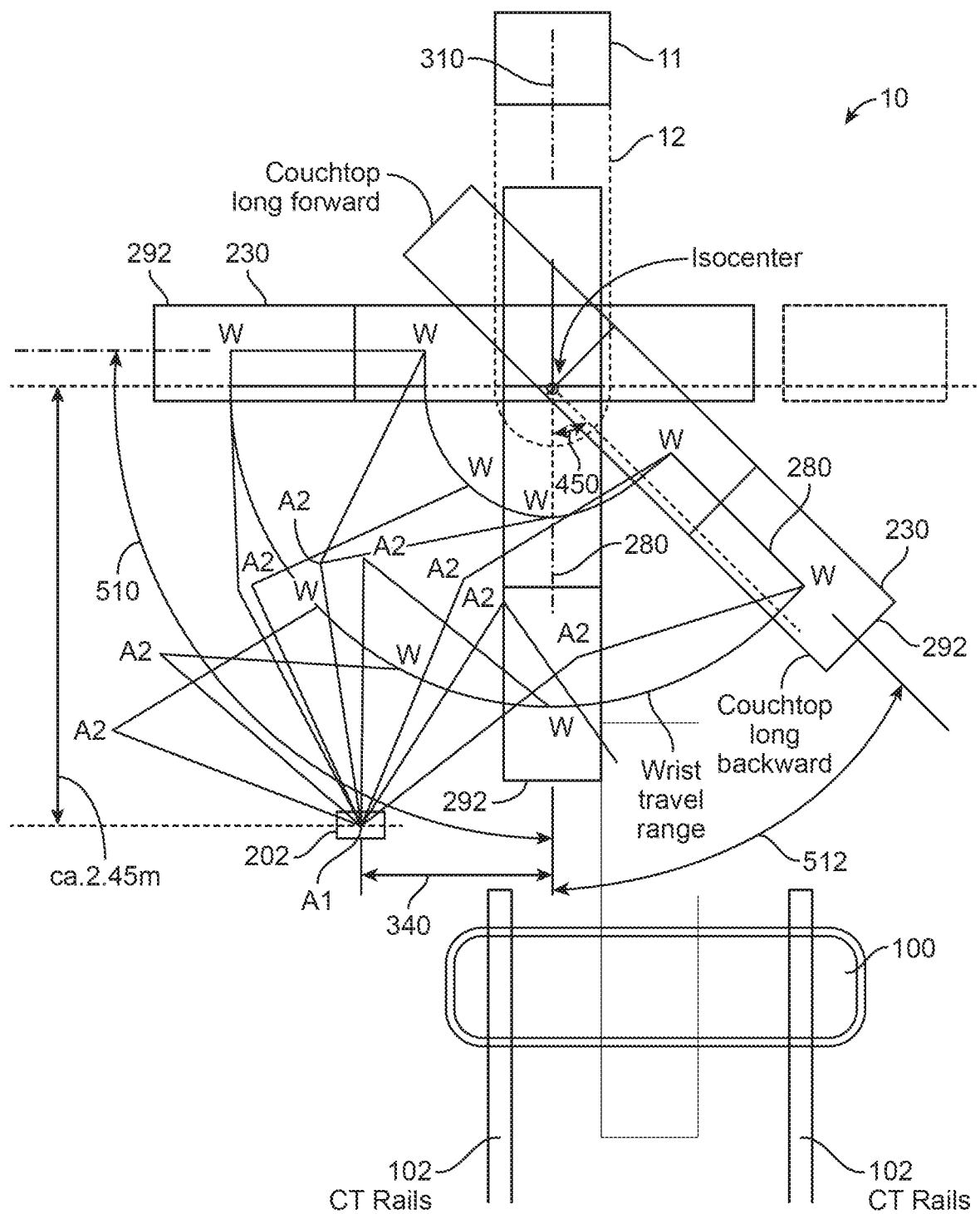
FIG. 8 illustrates a medical system having a treatment machine and an imaging machine facing each other, and a patient supporting device between the treatment machine and the imaging machine.

In the above embodiments, the medical system 10 is illustrated as having the treatment machine 11 and the imaging machine 100 arranged in a side-by-side configuration in a same room. In other embodiments, instead of the side-by-side configuration, the treatment machine 11 and the imaging machine 600 may be placed next to each other in a front-to-front configuration (in which the front of the treatment machine 11 faces towards the front of the imaging machine 100) (FIG. 8). In such configuration, the base 202 of the patient supporting device 200 is fixedly mounted at a location that is offset from a center of the treatment machine 11 by the distance 340. In further embodiments, the treatment machine 11 and the imaging machine 600 may be placed next to each other at 90° (or other angles) with respect to each other. In still further embodiments, the medical system 10 may not include the imaging machine 100.

Figure 9:
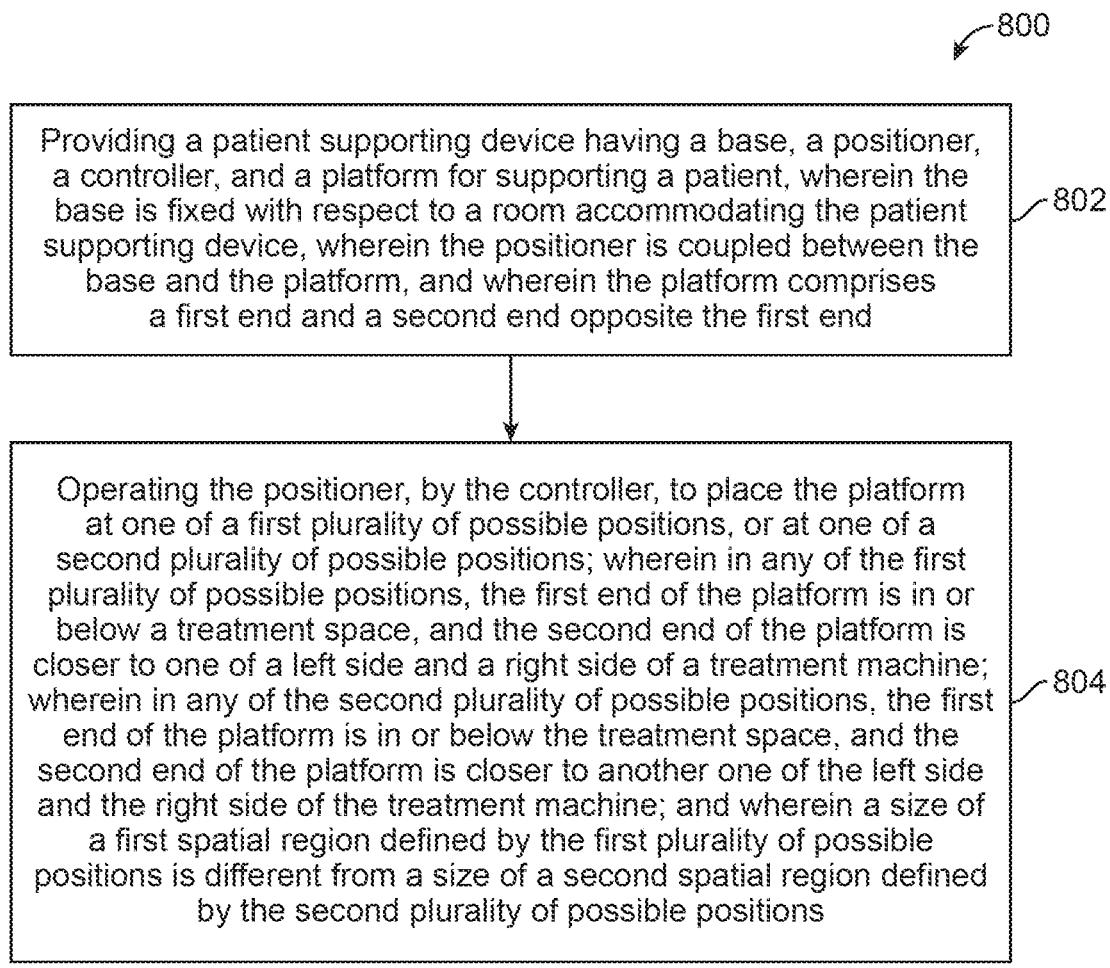
FIG. 9 illustrates a medical method in accordance with some embodiments.

FIG. 9 illustrates a medical method 800 in accordance with some embodiments. The medical method 800 includes providing a patient supporting device having a base, a positioner, a controller, and a platform for supporting a patient, wherein the base is fixed with respect to a room accommodating the patient supporting device, wherein the positioner is coupled between the base and the platform, and wherein the platform comprises a first end and a second end opposite the first end (item 802). The medical method 800 also includes operating the positioner, by the controller, to place the platform at one of a first plurality of possible positions, or at one of a second plurality of possible positions; wherein in any of the first plurality of possible positions, the first end of the platform is in or below a treatment space, and the second end of the platform is closer to one of a left side and a right side of a treatment machine; and wherein in any of the second plurality of possible positions, the first end of the platform is in or below the treatment space, and the second end of the platform is closer to another one of the left side and the right side of the treatment machine; and wherein a size of a first spatial region defined by the first plurality of possible positions is different from a size of a second spatial region defined by the second plurality of possible positions (item 804).

Optionally, in the medical method 800, the positioner comprises a first member rotatable relative the base about a first vertical axis, a second member rotatable relative to the first member about a second vertical axis, wherein the platform is rotatable relative to the second member about a third vertical axis.

Optionally, in the medical method 800, the positioner is operated to rotate the platform relative to the second member about the third vertical axis.

Optionally, in the medical method 800, the positioner is operated to rotate the second member relative to the first member about the second vertical axis.

Optionally, in the medical method 800, the positioner is operated to rotate the first member relative to the base about the first vertical axis.

Optionally, in the medical method 800, the positioner is operated to move the platform vertically.

Optionally, in the medical method 800, the positioner is operated to rotate the platform about a vertical axis while a first part of the platform is maintained under an isocenter.

Optionally, in the medical method 800, the platform is placed at an orientation with respect to the treatment machine, and wherein when the platform is at the orientation, a longitudinal axis of the platform forms an acute angle with respect to a machine axis that extends from a front of the treatment machine to a back of the treatment machine.

Optionally, the medical method 800 further includes rotating an energy output at the treatment machine while the platform is at the orientation.

Optionally, in the medical method 800, the positioner is operated by the controller to place the patient at an imaging position with respect to an imaging machine.

Optionally, in the medical method 800, the treatment machine and the imaging machine are in a side-by-side configuration.

Optionally, in the medical method 800, the treatment machine and the imaging machine are in a front-to-front configuration.

Optionally, in the medical method 800, the imaging machine comprises a CT machine, a x-ray machine, a fluoroscope, a MRI machine, an ultrasound device, a PET machine, a SPECT machine, or a PET-CT machine.

Optionally, the medical method 800 further includes delivering treatment radiation by the treatment machine.

Optionally, the medical method 800 further includes delivering a proton beam by the treatment machine.

Optionally, the medical method 800 further includes: operating the positioner, by the controller, to move the platform in accordance with a first movement scheme when the platform is in a first coordinate system associated with the treatment machine; and operating the positioner, by the controller, to move the platform in accordance with a second movement scheme when the platform is in a second coordinate system associated with the imaging machine, the second movement scheme being different from the first movement scheme.

Optionally, in the medical method 800, the positioner is operated, by the controller, to move a first part of the platform below an isocenter of the treatment machine, wherein the first part of the platform is closer to the first end of the platform than to the second end of the platform.

Optionally, the positioner is operated by the controller to move the platform during delivery of treatment energy by the treatment machine.

Optionally, the positioner is operated by the controller to move the platform in synchronization with a treatment energy out of the treatment machine to implement extended source-to-axis distance (SAD), reduced SAD, or variable SAD.

Specialized Processing System

Figure 10:
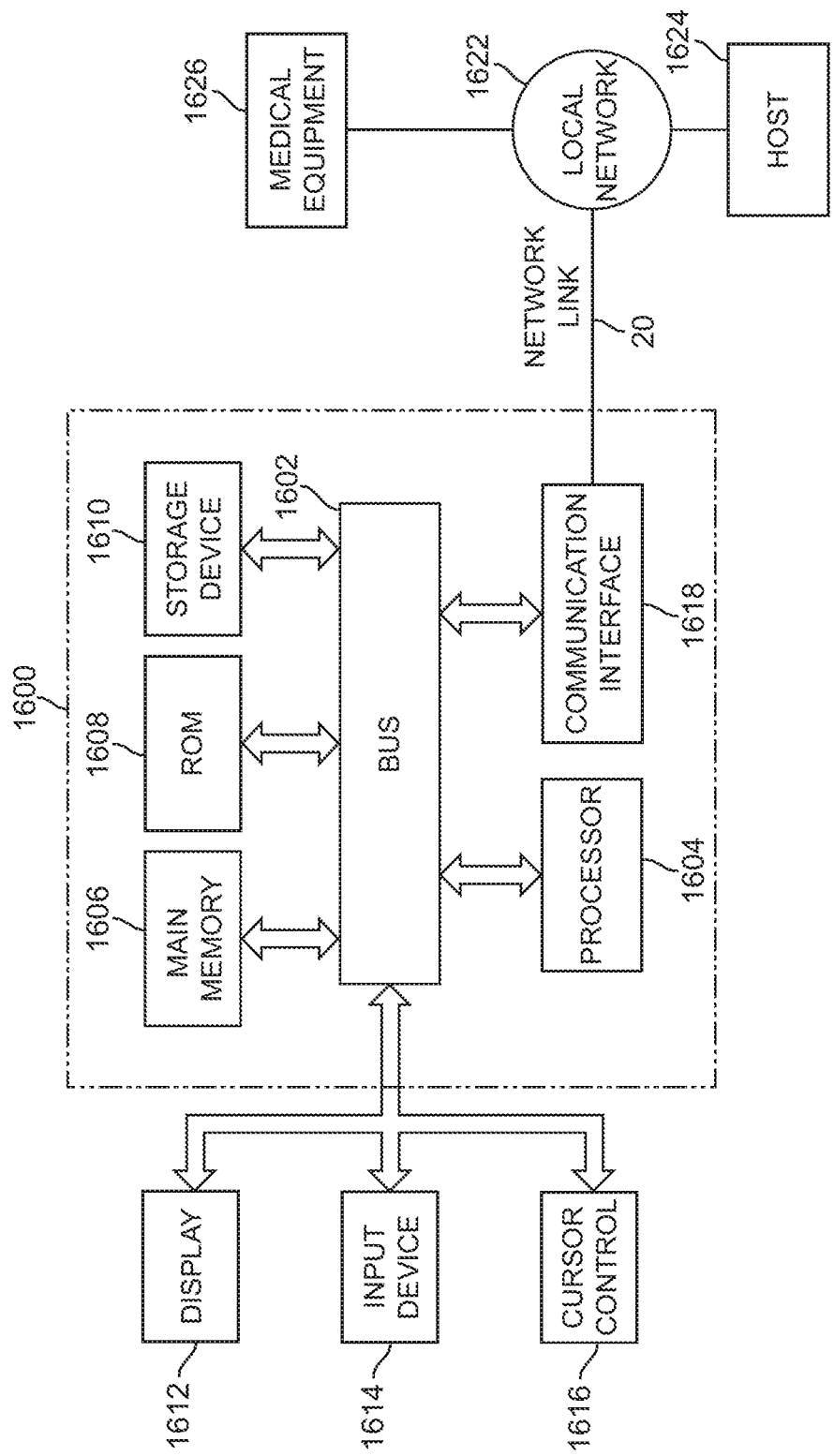
FIG. 10 is a block diagram of a specialized processing system.

FIG. 10 is a block diagram illustrating an embodiment of a specialized processing system 1600 that can be used to implement various embodiments described herein. For example, the processing system 1600 may be configured to operate the patient supporting device 200 in accordance with some embodiments. Also, in some embodiments, the processing system 1600 may be used to implement the controller 206 of the patient supporting device 200 and/or the processing unit 54 of FIG. 1. The controller 206 for the patient supporting device 200 may be the control 40 in some embodiments, or may be another control that is in communication with the positioner 204 of the patient supporting device 200. The processing system 1600 may also be an example of any processor described herein.

Processing system 1600 includes a bus 1602 or other communication mechanism for communicating information, and a processor 1604 coupled with the bus 1602 for processing information. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processor system 1600 may be coupled via the bus 1602 to a display 167, such as a flat panel, for displaying information to a user. An input device 1614, including alphanumeric and other keys, or a touchscreen, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a network, such as the Internet or a local network. A receiving unit local to the processing system 1600 can receive the data from the network, and provide the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

The following items are exemplary features of embodiments described herein. Each item may be an embodiment itself or may be a part of an embodiment. One or more items described below may be combined with other item(s) in an embodiment.

Item 1: A patient supporting device for supporting a patient includes: a base configured to be fixedly coupled to a room; a positioner mechanically coupled to the base; a platform mechanically coupled to the positioner, wherein the platform has a first end and a second end opposite the first end; and a controller configured to operate the positioner; wherein the positioner is operable by the controller to place the platform at one of a first plurality of possible positions, wherein in any of the first plurality of possible positions, the first end of the platform is in or below a treatment space, and the second end of the platform is closer to one of a left side and a right side of a treatment machine; wherein the positioner is also operable by the controller to place the platform at one of a second plurality of possible positions, wherein in any of the second plurality of possible positions, the first end of the platform is in or below the treatment space, and the second end of the platform is closer to another one of the left side and the right side of the treatment machine; and wherein a size of a first spatial region defined by the first plurality of possible positions is different from a size of a second spatial region defined by the second plurality of possible positions.

Item 2: The first spatial region has an angular range of more than 60°.

Item 3: The first spatial region has an angular range that is anywhere between 70° and 110°.

Item 4: The second spatial region has an angular range of less than 60°.

Item 5: The second spatial region has an angular range that is anywhere between 35° and 55°.

Item 6: The positioner comprises: a first member having a first end and a second end, wherein the first end of the first member is rotatably coupled to the base so that the first member is rotatable relative to the base about a first vertical axis; a second member having a first end and a second end, wherein the first end of the second member is rotatably coupled to the second end of the first member so that the second member is rotatable relative to the first member about a second vertical axis; wherein the platform is rotatably coupled to the second end of the second member so that the platform is rotatable relative to the second member about a third vertical axis.

Item 7: The second member comprises a first member portion and a second member portion, the first member portion comprising the first end of the second member, the second member portion comprising the second end of the second member, wherein the second member portion is rotatably coupled to the first member portion so that the second member portion is rotatable relative to the first member portion about a first horizontal axis.

Item 8: The platform is rotatably coupled to the second member portion so that the platform is rotatable relative to the second member portion about a second horizontal axis.

Item 9: A rotation of the platform relative to the second member portion about the second horizontal axis, and a rotation of the second member portion relative to the first member portion about the first horizontal axis, are synchronized to move the platform vertically.

Item 10: The platform comprises a longitudinal axis, and the positioner is configured to tilt the platform about the longitudinal axis.

Item 11: The patient supporting device further includes one or more cameras coupled to the platform.

Item 12: The platform is detachably coupled to the positioner.

Item 13: The patient supporting device further includes a user interface configured for allowing an operator to enter one or more commands to control a positioning and/or movement of the platform.

Item 14: The positioner is also operable by the controller to place a first part of the platform below an isocenter of the treatment machine, the first part of the platform being closer to the first end of the platform than to the second end of the platform.

Item 15: The controller is configured to operate the positioner to move the platform during delivery of treatment energy by the treatment machine.

Item 16: The controller is configured to operate the positioner to move the platform in synchronization with a treatment energy out of the treatment machine to implement extended source-to-axis distance (SAD), reduced SAD, or variable SAD.

Item 17: A medical system includes the patient supporting device, and the treatment machine, wherein the patient supporting device is configured to place the patient at a treatment position with respect to the treatment machine.

Item 18: The positioner is operable by the controller to place a first part of the platform under an isocenter, and to move the second end of the platform along a horizontal path while maintaining the first part of the platform under the isocenter.

Item 19: The patient supporting device is configured to place the platform at an orientation with respect to the treatment machine, and wherein when the platform is at the orientation, a longitudinal axis of the platform forms an acute angle with respect to a machine axis that extends from a front of the treatment machine to a back of the treatment machine.

Item 20: The treatment machine is configured to rotate an energy output while the platform is at the orientation.

Item 21: The medical system further includes an imaging machine, wherein the patient supporting device is configured to place the patient at an imaging position with respect to the imaging machine.

Item 22: The treatment machine and the imaging machine are in a side-by-side configuration.

Item 23: The treatment machine and the imaging machine are in a front-to-front configuration.

Item 24: The imaging machine comprises a CT machine, a x-ray machine, a fluoroscope, a MRI machine, an ultrasound device, a PET machine, a SPECT machine, or a PET-CT machine.

Item 25: The patient supporting device is configured to move the platform in accordance with a first movement scheme when the platform is in a first coordinate system associated with the treatment machine, and to move the platform in accordance with a second movement scheme when the platform is in a second coordinate system associated with the imaging machine, the second movement scheme being different from the first movement scheme.

Item 26: The treatment machine comprises a radiation treatment machine.

Item 27: The radiation treatment machine comprises a ring gantry.

Item 28: The radiation treatment machine comprises an arm having an energy output and a collimator.

Item 29: The treatment machine comprises a proton treatment machine.

Item 30: A medical method includes: providing a patient supporting device having a base, a positioner, a controller, and a platform for supporting a patient, wherein the base is fixed with respect to a room accommodating the patient supporting device, wherein the positioner is coupled between the base and the platform, and wherein the platform comprises a first end and a second end opposite the first end; and operating the positioner, by the controller, to place the platform at one of a first plurality of possible positions, or at one of a second plurality of possible positions; wherein in any of the first plurality of possible positions, the first end of the platform is in or below a treatment space, and the second end of the platform is closer to one of a left side and a right side of a treatment machine; wherein in any of the second plurality of possible positions, the first end of the platform is in or below the treatment space, and the second end of the platform is closer to another one of the left side and the right side of the treatment machine; and wherein a size of a first spatial region defined by the first plurality of possible positions is different from a size of a second spatial region defined by the second plurality of possible positions.

Item 31: The positioner comprises a first member rotatable relative the base about a first vertical axis, a second member rotatable relative to the first member about a second vertical axis, wherein the platform is rotatable relative to the second member about a third vertical axis.

Item 32: The positioner is operated to rotate the platform relative to the second member about the third vertical axis.

Item 33: The positioner is operated to rotate the second member relative to the first member about the second vertical axis.

Item 34: The positioner is operated to rotate the first member relative to the base about the first vertical axis.

Item 35: The positioner is operated to move the platform vertically.

Item 36: The positioner is operated to rotate the platform about a vertical axis while a first part of the platform is maintained under an isocenter.

Item 37: The platform is placed at an orientation with respect to the treatment machine, and wherein when the platform is at the orientation, a longitudinal axis of the platform forms an acute angle with respect to a machine axis that extends from a front of the treatment machine to a back of the treatment machine.

Item 38: The medical method further includes rotating an energy output at the treatment machine while the platform is at the orientation.

Item 39: The positioner is operated by the controller to place the patient at an imaging position with respect to an imaging machine.

Item 40: The treatment machine and the imaging machine are in a side-by-side configuration.

Item 41: The treatment machine and the imaging machine are in a front-to-front configuration.

Item 42: The imaging machine comprises a CT machine, a x-ray machine, a fluoroscope, a MRI machine, an ultrasound device, a PET machine, a SPECT machine, or a PET-CT machine.

Item 43: The medical method further includes delivering treatment radiation by the treatment machine.

Item 44: The medical method further includes delivering a proton beam by the treatment machine.

Item 45: The medical method further includes: operating the positioner, by the controller, to move the platform in accordance with a first movement scheme when the platform is in a first coordinate system associated with the treatment machine; and operating the positioner, by the controller, to move the platform in accordance with a second movement scheme when the platform is in a second coordinate system associated with the imaging machine, the second movement scheme being different from the first movement scheme.

Item 46: The positioner is operated, by the controller, to move a first part of the platform below an isocenter of the treatment machine, wherein the first part of the platform is closer to the first end of the platform than to the second end of the platform.

Item 47: The positioner is operated by the controller to move the platform during delivery of treatment energy by the treatment machine.

Item 48: The positioner is operated by the controller to move the platform in synchronization with a treatment energy out of the treatment machine to implement extended source-to-axis distance (SAD), reduced SAD, or variable SAD.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A patient supporting device for supporting a patient, comprising:
   a base configured to be fixedly mounted with respect to a floor of a room;
   a positioner mechanically coupled to the base;
   a platform mechanically coupled to the positioner, wherein the platform has a first end and a second end opposite the first end; and
   a controller configured to operate the positioner;
   wherein the positioner is operable by the controller to place the platform at one of a first plurality of possible positions, wherein in any of the first plurality of possible positions, the first end of the platform is in or below a treatment space, and the second end of the platform is closer to one of a left side and a right side of a treatment machine;
   wherein the positioner is also operable by the controller to place the platform at one of a second plurality of possible positions, wherein in any of the second plurality of possible positions, the first end of the platform is in or below the treatment space, and the second end of the platform is closer to another one of the left side and the right side of the treatment machine; and
   wherein a size of a first spatial region defined by the first plurality of possible positions is different from a size of a second spatial region defined by the second plurality of possible positions.

2. The patient supporting device of claim 1, wherein the first spatial region has an angular range of more than 60°.

3. The patient supporting device of claim 1, wherein the second spatial region has an angular range of less than 60°.

4. The patient supporting device of claim 1, wherein the positioner comprises:
   a first member having a first end and a second end, wherein the first end of the first member is rotatably coupled to the base so that the first member is rotatable relative to the base about a first vertical axis; and
   a second member having a first end and a second end, wherein the first end of the second member is rotatably coupled to the second end of the first member so that the second member is rotatable relative to the first member about a second vertical axis;
   wherein the platform is rotatably coupled to the second end of the second member so that the platform is rotatable relative to the second member about a third vertical axis.

5. The patient supporting device of claim 4, wherein the second member comprises a first member portion and a second member portion, the first member portion comprising the first end of the second member, the second member portion comprising the second end of the second member, wherein the second member portion is rotatably coupled to the first member portion so that the second member portion is rotatable relative to the first member portion about a first horizontal axis.

6. The patient supporting device of claim 5, wherein the platform is rotatably coupled to the second member portion so that the platform is rotatable relative to the second member portion about a second horizontal axis.

7. The patient supporting device of claim 6, wherein a rotation of the platform relative to the second member portion about the second horizontal axis, and a rotation of the second member portion relative to the first member portion about the first horizontal axis, are synchronized to move the platform vertically.

8. The patient supporting device of claim 1, further comprising a user interface configured for allowing an operator to enter one or more commands to control a positioning and/or movement of the platform.

9. The patient support device of claim 1, wherein the positioner is also operable by the controller to place a first part of the platform below an isocenter of the treatment machine, the first part of the platform being closer to the first end of the platform than to the second end of the platform.

10. The patient supporting device of claim 1, wherein the controller is configured to operate the positioner to move the platform during delivery of treatment energy by the treatment machine.

11. The patient supporting device of claim 1, wherein the controller is configured to operate the positioner to move the platform in synchronization with a treatment energy out of the treatment machine to implement extended source-to-axis distance (SAD), reduced SAD, or variable SAD.

12. A medical system comprising the patient supporting device of claim 1, and the treatment machine, wherein the patient supporting device is configured to place the patient at a treatment position with respect to the treatment machine.

13. The medical system of claim 12, wherein the positioner is operable by the controller to place a first part of the platform under an isocenter, and to move the second end of the platform along a horizontal path while maintaining the first part of the platform under the isocenter.

14. The medical system of claim 12, wherein the patient supporting device is configured to place the platform at an orientation with respect to the treatment machine, and wherein when the platform is at the orientation, a longitudinal axis of the platform forms an acute angle with respect to a machine axis that extends from a front of the treatment machine to a back of the treatment machine.

15. The medical system of claim 12, further comprising an imaging machine, wherein the patient supporting device is configured to place the patient at an imaging position with respect to the imaging machine.

16. The medical system of claim 15, wherein the treatment machine and the imaging machine are in a side-by-side configuration.

17. The medical system of claim 15, wherein the treatment machine and the imaging machine are in a front-to-front configuration.

18. The medical system of claim 15, wherein the imaging machine comprises a CT machine, a x-ray machine, a fluoroscope, a MRI machine, an ultrasound device, a PET machine, a SPECT machine, or a PET-CT machine.

19. The medical system of claim 15, wherein the patient supporting device is configured to move the platform in accordance with a first movement scheme when the platform is in a first coordinate system associated with the treatment machine, and to move the platform in accordance with a second movement scheme when the platform is in a second coordinate system associated with the imaging machine, the second movement scheme being different from the first movement scheme.

20. A medical method, comprising:
providing a patient supporting device having a base, a positioner, a controller, and a platform for supporting a patient, wherein the base is fixedly with mounted respect to a floor of a room accommodating the patient supporting device, wherein the positioner is coupled between the base and the platform, and wherein the platform comprises a first end and a second end opposite the first end; and operating the positioner, by the controller, to place the platform at one of a first plurality of possible positions, or at one of a second plurality of possible positions;
wherein in any of the first plurality of possible positions, the first end of the platform is in or below a treatment space, and the second end of the platform is closer to one of a left side and a right side of a treatment machine;
wherein in any of the second plurality of possible positions, the first end of the platform is in or below the treatment space, and the second end of the platform is closer to another one of the left side and the right side of the treatment machine; and
wherein a size of a first spatial region defined by the first plurality of possible positions is different from a size of a second spatial region defined by the second plurality of possible positions.

21. The medical method of claim 20, wherein:
the operating the positioner includes,
moving the platform in accordance with a first movement scheme when the platform is in a first coordinate system associated with the treatment machine, and
moving the platform in accordance with a second movement scheme when the platform is in a second coordinate system associated with an imaging machine, the second movement scheme being different from the first movement scheme; and
the treatment machine and the imaging machine are in a side-by-side configuration or a front-to-front configuration.

* * * * *